(12) United States Patent
Matsufuji et al.

(10) Patent No.: US 11,089,806 B2
(45) Date of Patent: Aug. 17, 2021

(54) FLAVOR IMPROVEMENT METHOD FOR YEAST CELLS AND FOOD QUALITY IMPROVING AGENT

(71) Applicant: TableMark Co., Ltd., Tokyo (JP)

(72) Inventors: Hisashi Matsufuji, Yokohama (JP); Tsuyoshi Yanagishita, Yokohama (JP); Yusuke Tanaka, Yokohama (JP); Yoshitaka Haishima, Tokyo (JP); Hidenori Okuhama, Tokyo (JP); Shigenori Takano, Tokyo (JP); Takeo Inoue, Tokyo (JP)

(73) Assignee: TABLEMARK CO., LTD., Tokyo (JP)

( * ) Notice: Subject to any disclaimer, the term of this patent is extended or adjusted under 35 U.S.C. 154(b) by 3 days.

(21) Appl. No.: 15/527,131

(22) PCT Filed: Nov. 19, 2015

(86) PCT No.: PCT/JP2015/082560
§ 371 (c)(1),
(2) Date: May 16, 2017

(87) PCT Pub. No.: WO2016/080490
PCT Pub. Date: May 26, 2016

(65) Prior Publication Data
US 2017/0347697 A1 Dec. 7, 2017

(30) Foreign Application Priority Data
Nov. 19, 2014 (JP) .............................. JP2014-234916

(51) Int. Cl.
| A23L 33/14 | (2016.01) |
| A23L 13/00 | (2016.01) |
| A23L 33/17 | (2016.01) |
| A23L 17/00 | (2016.01) |
| A23L 33/21 | (2016.01) |
| C12N 1/18 | (2006.01) |
| C12N 1/16 | (2006.01) |
| C12N 9/42 | (2006.01) |
| C12N 9/54 | (2006.01) |

(52) U.S. Cl.
CPC .............. *A23L 33/14* (2016.08); *A23L 13/00* (2016.08); *A23L 17/00* (2016.08); *A23L 33/17* (2016.08); *A23L 33/21* (2016.08); *C12N 1/16* (2013.01); *C12N 1/18* (2013.01); *C12N 9/2437* (2013.01); *C12N 9/54* (2013.01); *C12Y 302/01004* (2013.01); *C12Y 304/00* (2013.01); *A23V 2002/00* (2013.01)

(58) Field of Classification Search
CPC .......... A23L 33/14; A23L 33/17; A23L 33/21; A23L 33/35; A23L 35/10; A23L 13/00; A23L 17/00; C12Y 304/00
USPC ........................................................ 426/60
See application file for complete search history.

(56) References Cited

U.S. PATENT DOCUMENTS

| 3,809,776 A * | 5/1974 | Chao ........................ C12N 1/08 426/431 |
| 4,089,978 A | 5/1978 | Lugay et al. |
| 4,264,628 A * | 4/1981 | Hill ........................ C12N 1/063 426/7 |
| 2006/0110402 A1* | 5/2006 | Eguchi ................ C05G 3/0041 424/195.16 |
| 2006/0263415 A1* | 11/2006 | Sedmak .................. A61P 29/00 424/442 |
| 2010/0183767 A1* | 7/2010 | Noordam ............... C12N 1/063 426/60 |
| 2014/0308430 A1* | 10/2014 | Ason ........................ A23J 1/18 426/650 |

FOREIGN PATENT DOCUMENTS

| CN | 101720905 A | 6/2010 |
| DE | 10 2011 017 405 A1 | 10/2012 |
| EP | 2 534 964 A1 | 12/2012 |
| EP | 2 774 993 A1 | 9/2014 |
| JP | 55-150861 A | 11/1980 |
| JP | 59-183671 A | 10/1984 |
| JP | 4-131064 A | 5/1992 |
| JP | 4-248968 A | 9/1992 |
| JP | 6-141804 A | 5/1994 |
| JP | 7-184640 A | 7/1995 |
| JP | 9-56361 A | 3/1997 |
| JP | 11-318351 A | 11/1999 |
| JP | 2002-153263 A | 5/2002 |
| JP | 2003-197 A | 1/2003 |
| JP | 2004-275083 A | 10/2004 |
| JP | 2006-288267 A | 10/2006 |
| JP | 2007-523940 A | 8/2007 |
| JP | 2007-295920 A | 11/2007 |
| JP | 2009-159997 A | 7/2009 |
| JP | 2014-79197 A | 10/2012 |

(Continued)

OTHER PUBLICATIONS

JP-2014-079179—English Abstract—pp. 8-9 (Year: 2014).*
Extended European Search Report dated Oct. 24, 2018, in European Patent Application No. 15862002.1.
International Search Report for PCT/JP2015/082560 dated Dec. 28, 2015.
Written Opinion of the International Searching Authority for PCT/JP2015/082560 (PCT/ISA/237) dated Dec. 28, 2015.
Al-Kadamany et al., "Estimation of shelf-life of concentrated yogurt by monitoring selected microbiological and physicochemical changes during storage," Lebensm.-Wiss. U.-Technol. (2003), vol. 36, pp. 407-414.

(Continued)

*Primary Examiner* — Hamid R Badr
(74) *Attorney, Agent, or Firm* — Birch, Stewart, Kolasch & Birch, LLP

(57) ABSTRACT

The present invention provides a method of improving the taste of yeast cells including a step of reacting the yeast cells with protease or cellulase, and a quality improving material for food containing yeast cells as an active ingredient in which the taste is improved by the method of improving the taste.

13 Claims, 5 Drawing Sheets

(56) References Cited

FOREIGN PATENT DOCUMENTS

| WO | WO 2005/082927 A2 | 9/2005 |
|----|-------------------|--------|
| WO | WO 2006/121803 A1 | 11/2006 |

OTHER PUBLICATIONS

Communication Pursuant to Rule 164(1) EPC dated Apr. 20, 2018, in European Patent Application No. 15862002.1.
Satrapai, S. and M. Suphantharika, "Influence of spent bewer's yeast β-glucan on gelatinization and retrogradation of rice starch," Carbohydrate Polymers (2007), vol. 67, pp. 500-510.
Chinese Office Action in counterpart CN Application No. 201580062434.7 dated Jan. 29, 2021 with English Translation.
Communication Pursuant to Article 94(3)EPC issued Nov. 4, 2019, in European Patent Application No. 15 862 002.1.

\* cited by examiner

FLAVOR IMPROVEMENT METHOD FOR YEAST CELLS AND FOOD QUALITY IMPROVING AGENT

TECHNICAL FIELD

The present invention relates to a method of improving the taste of yeast cells and a quality improving material for food. Priority is claimed on Japanese Patent Application No. 2014-234916, filed Nov. 19, 2014, the content of which is incorporated herein by reference.

BACKGROUND ART

A yeast extract obtained by extracting taste ingredients or nutrients from yeast is widely used as a safe and high quality natural seasoning, a nutrient source for cultivating various microorganisms, a nutrient source for microorganisms effective for soil improvement. In addition, as the yeast extract containing a high concentration of a specific ingredient is extracted from yeast, a large amount of a yeast extract residue in which a useful ingredient remains is produced. The yeast extract residue is composed of almost complete yeast cells. Such yeast cells are also produced in the manufacture of alcoholic beverages such as beer.

However, since yeast cells have an undesirable taste and smell, they are limited to certain applications, and except for some used for nutritional foods or fertilizers, most of them are discarded. Therefore, effective use of yeast cells is being investigated.

For example, Patent Literature 1 discloses a method of decolorizing and deodorizing an extraction residue of a yeast extract, the method comprising mixing an alkali such as sodium hydroxide and a bleaching agent such as hydrogen peroxide with the extraction residue of the yeast extract, and heating the resulting mixture.

Patent Literature 1 also discloses a method of decolorizing and deodorizing an extraction residue of a yeast extract, which is characterized by treating an extraction residue of a yeast extract, the residue obtained after the extraction of the yeast extract from yeast and containing a yeast cell wall as a major ingredient, with an alkali and an acid, and then treating the resulting extraction residue with ozone gas at a concentration of 1000 to 20000 ppm for 1 to 120 minutes and with ethanol once before or after the ozone treatment or twice before and after the ozone treatment.

Also, for example, Patent Literature 2 discloses a method of treating a yeast extract residue, which is characterized by solubilizing a yeast extract residue using a culture solution of bacteria producing a yeast-lyzing enzyme (YLase), and treating the resulting solubilized liquid by an anaerobic wastewater treatment method.

CITATION LIST

Patent Literature

[Patent Literature 1]
  Japanese Unexamined Patent Application, First Publication No. H4-248968
[Patent Literature 2]
  Japanese Unexamined Patent Application, First Publication No. H7-184640

SUMMARY OF INVENTION

Technical Problem

However, according to the conventional treatment methods, in some cases, sufficient improvement in taste was not achieved since yeast cells still had an undesirable taste and smell. For this reason, the use of yeast cells as a food material such as a quality improving material for food was limited.

Therefore, an object of the present invention is to provide a more effective method of improving the taste of yeast cells. Another object of the present invention is to provide a quality improving material for food containing yeast cells with improved taste as an active ingredient.

Solution to Problem

The present invention is as follows.

(1) A method of improving the taste of yeast cells, including reacting a protease and/or cellulase with yeast cells.

(2) The method described in (1), further including, before or after the reaction of the protease and/or cellulase, adding an emulsifier to the yeast cells.

(3) The method described in (2), in which the emulsifier has a Hydrophile-Lipophile Balance (HLB) value of 1 to 14.

(4) The method described in (2) or (3), in which the emulsifier is one or a mixture of two or more types of compounds selected from the group consisting of glycerin fatty acid esters, sorbitan fatty acid esters, propylene glycol fatty acid esters, sucrose fatty acid esters, lecithins and saponins.

(5) The method described in any one of (1) to (4), in which the yeast cells are a yeast extract residue.

(6) The method described in any one of (1) to (5), in which the protease is an endo-type protease.

(7) The method described in (6), in which the endo-type protease is derived from *Bacillus amyloliquefaciens*.

(8) A quality improving material for food including the yeast cells improved in taste by the method of improving the taste of yeast cells described in any one of (1) to (7) as an active ingredient.

(9) The quality improving material for food described in (8), including proteins at 25% by mass or more, β-glucans at 10% by mass or more, and dietary fiber at 25% by mass or more.

(10) A powder mixture, including the quality improving material for food described in (8) or (9) as an active ingredient.

(11) Batter, including the quality improving material for food described in (8) or (9) as an active ingredient.

(12) Fried food, including the quality improving material for food described in (8) or (9).

(13) A softener for meat or seafood, including the quality improving material for food described in (8) or (9) as an active ingredient.

(14) A method of softening meat or seafood, including contacting the quality improving material for food described in (8) or (9) with meat or seafood.

(15) A method for preventing syneresis or oil separation of processed food, including contacting the quality improving material for food described in (8) or (9) with a food material.

Advantageous Effects of Invention

The present invention can provide a more effective method of improving the taste of yeast cells. In addition, the present invention provides a quality improving material for food containing yeast cells with improved taste as an active ingredient.

DESCRIPTION OF EMBODIMENTS

[Method of Improving Taste]

Figure 1:
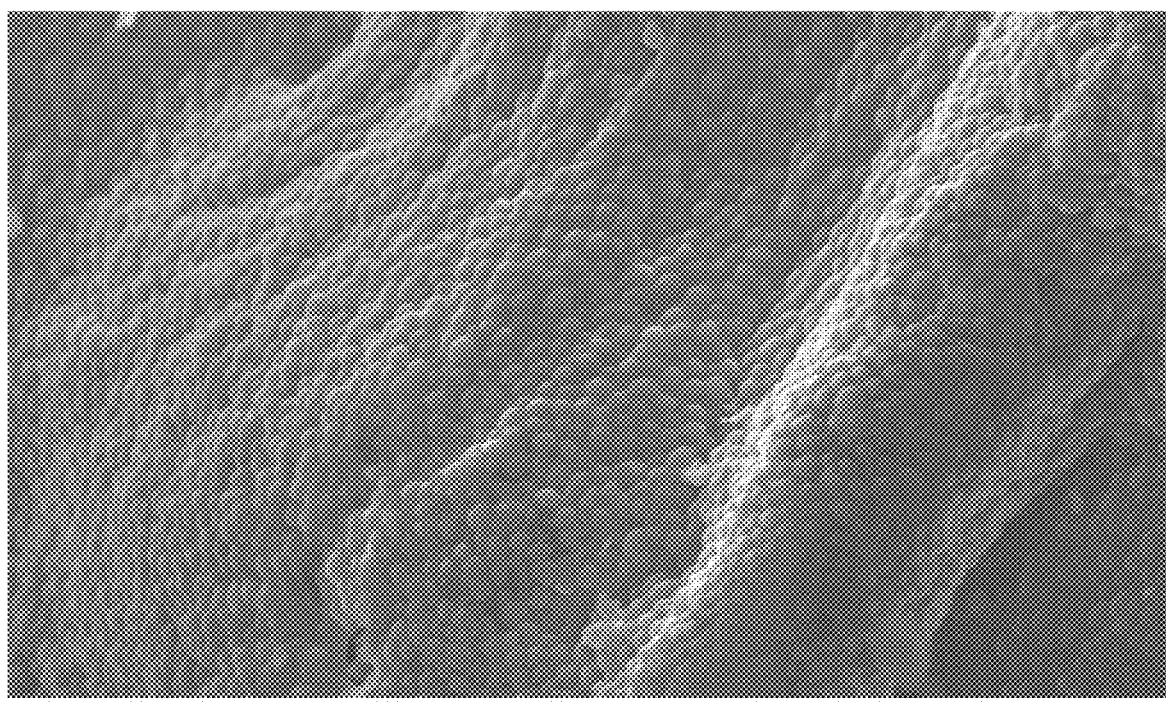
FIG. 1 is an electron micrograph of a sample (yeast cells) in Preparation Example 8.

According to an embodiment, the present invention provides a method of improving the taste of yeast cells, the method including reacting yeast cells with a protease or cellulase. The method of improving the taste according to the embodiment may also be a method of preparing yeast cells with improved taste, the method including treating yeast cells with a protease and/or cellulase.

According to the method of the embodiment, the taste of yeast cells may be improved. Therefore, the yeast cells can be added to food, and also effectively used. In addition, since the method of the embodiment is possibly carried out without using harmful organic solvents or expensive machines, it is low-cost and environmentally considered.

(Yeast Cells)

According to the method of the embodiment, examples of the yeast cells may include cells of torula yeast, baker's yeast, beer yeast, sake yeast, and the like. In addition, the yeast cells may be present in various forms such as compressed yeast, dry yeast, active dry yeast, dead yeast, sterilized dry yeast, and the like. The yeast cells may also be a yeast cell-derived material (for example, a yeast cell lysate or powder) having substantially the same composition as yeast cells (microbial cells).

The yeast cells used in the present invention may be prepared in various forms such as dry yeast cells, a dehydrated yeast product, a cell suspension, or the like. In terms of convenience and ease in preservation, stability, transportation/storage, handling or administration as food, feed or medicine, the yeast cells are preferably prepared in the form of sterilized dry yeast.

The yeast used in the present invention may be, for example, yeast belonging to the genus *Saccharomyces* or *Candida*, but the present invention is not limited thereto. For example, in terms of abundant dietary experience, *Saccharomyces cerevisiae* may be used, or in terms of much information obtained by research or the like, *Candida utilis* may be used.

The yeast cells may be cells that do not undergo a fermentation process because they contain a low ratio of materials causing an undesirable taste or smell, and facilitate the achievement of a taste-improving effect according to the method of the embodiment, and are preferably torula yeast or baker's yeast.

The yeast cells may also be an extraction residue of a yeast extract. Here, the extraction residue of a yeast extract refers to an ingredient remaining after a yeast extract is extracted from yeast. Examples of a method of extracting the yeast extract may include, but are not particularly limited to, a hydrothermal treatment method, a self-digestion method, an enzyme decomposition method and the like.

(Protease)

Examples of the proteases may include a serine protease, a cysteine protease, an aspartic protease, a metalloprotease and the like, and for example, a microorganism-derived protease, a plant-derived papain, bromelain, animal-derived trypsin, pepsin, cathepsin and the like.

Examples of the microorganisms may include, for example, the genus *Aspergillus* including *Aspergillus oryzae*, *Aspergillus melleus* and the like; the genus *Rhizopus* including *Rhizopus niveus*, *Rhizopus oryzae* and the like; and the genus *Bacillus* including *Bacillus amyloliquefaciens*, *Bacillus licheniformis*, *Bacillus stearothermophilus* and the like. Among them, in terms of easily obtaining a taste-improving effect according to the method of the embodiment, a protease derived from *Bacillus amyloliquefaciens* is preferable.

The protease may be an endo-type protease or an exo-type protease, but in terms of easily achieving a taste-improving effect according to the method of the embodiment, an endo-type protease is preferable.

While not being bound by a particular theory, the inventors have assumed that the reaction of yeast cells with a protease achieves the cleavage of a protein on the surface of a yeast cell wall, and the removal of a lower alcohol or the like attached to the protein, which is a material causing an undesirable smell, thereby removing the undesirable smell, and results in the effect of improving the taste of the yeast cells.

(Cellulase)

The cellulase used herein may be any cellulase that hydrolyzes a glycosidic bond of a $\beta$-1,4-glucan such as cellulose, and examples of the cellulases may include, but are not particularly limited to, cellulases derived from microorganisms, such as the genus *Trichoderma* including *Trichoderma reesei*, *Trichoderma viride* and the like; the genus *Aspergillus* including *Aspergillus acleatus*, *Aspergillus niger* and the like; the genus *Clostridium* including *Clostridium thermocellum*, *Clostridium josui* and the like; the genus *Cellulomonas* including *Cellulomonas fimi* and the like; the genus *Acremonium* including *Acremonium celluloriticus* and the like; the genus *Irpex* including *Irpex lacteus* and the like; the genus *Humicola* including *Humicola insolens* and the like; and the genus *Pyrococcus* including *Pyrococcus horikoshii* and the like.

As will be described below, the inventors also found that the effect of improving the taste of yeast cells is achieved by reacting yeast cells with a cellulase.

While not being bound by a particular theory, the inventors have assumed that the reaction of yeast cells with a cellulase achieves the cleavage of polysaccharides constituting a yeast cell wall, and the removal of a lower alcohol attached to the cell wall, which is a material causing an undesirable smell, and results in the effect of improving the taste of the yeast cells.

(Improvement in Taste)

In the specification, improvement in taste refers to a reduction in an undesirable taste (a bitter, astringent, acrid taste or the like) or undesirable smell, which is the characteristic of yeast cells such as a yeast extract residue. As the taste of yeast cells is improved by the method of the embodiment, the yeast cells are able to be added to foods as a quality the improving material for food.

(Step of Reacting Yeast Cells with Protease and/or Cellulase)

In this step, a protease and/or cellulase is added to yeast cells to induce a reaction. The amount of the protease added may be 1 to 5000 units, preferably 10 to 2000 units, and more preferably 100 to 300 units per 1 g of the yeast cells (solid content).

In addition, the amount of the cellulase added may be 0.1 to 100 units, preferably 0.5 to 50 units, and more preferably 1 to 20 units per 1 g of the yeast cells (solid content).

When the amount of the added enzyme is too small, it is difficult to obtain a sufficient taste-improving effect. Contrarily, when the amount of the added enzyme is too large, it is disadvantageous in cost.

One or a mixture of two or more types of proteases may be reacted with the yeast cells. Likewise, one or a mixture of two or more types of cellulases may be reacted with the yeast cells. Alternatively, either of the protease or cellulase may be reacted with the yeast cells, or both of the protease and the cellulase may be reacted with the yeast cells.

The reaction temperature and time for the protease or cellulase may be suitably adjusted according to the selected enzyme. The reaction temperature may be, for example, 25 to 60° C. In addition, the reaction time may be, for example, 1 to 10 hours.

Modified Examples

In one embodiment, the method of improving the taste may further include adding an emulsifier to the yeast cells before or after the step of reacting the yeast cells with the protease and/or cellulase as described above.

When the emulsifier is added to the yeast cells, an undesirable taste such as a bitter, astringent, acrid taste or the like may be further reduced.

The step of adding the emulsifier may be carried out before or after the step of reacting the yeast cells with the protease and/or cellulase as described above. Alternatively, when both of the protease and the cellulase are reacted, the emulsifier may be added before the reaction with the protease or cellulase, between the reaction with any one of the protease and the cellulase and the reaction with the other, or after the reaction with the protease or cellulase. Even if the step of adding the emulsifier is performed at any time, it is possible to obtain the effect of further reducing an undesirable taste.

While not being bound by a particular theory, the inventors have assumed that, the addition of the emulsifier to the yeast cells facilitates the removal of materials causing an undesirable taste such as a bitter, astringent, acrid taste or the like, for example, hydrophobic amino acids and the like, during washing with water, and result in a reduction in an undesirable taste of the yeast cells.

In addition, the washing with water refers to the addition of water to the yeast cells to wash the cells through stirring. After the washing with water, solid-liquid separation is performed using a centrifugal separator or the like to remove solubilized materials and the like. By repeating the washing with water several times, ingredients causing an undesirable taste or smell may be removed.

(Emulsifier)

The emulsifier may have an HLB value of 1 to 14. The HLB value of the emulsifier is preferably 1 to 12, and more preferably 1 to 7.

Examples of the emulsifiers may include glycerin fatty acid esters, sorbitan esters of fatty acids, propylene glycol fatty acid esters, sucrose fatty acid esters, lecithins, saponins and the like. In addition, to the yeast cells, one type or a mixture of two or more types of the emulsifiers may be added.

Examples of the glycerin fatty acid esters may include monoglycerin fatty acid esters having a glycerin polymerization degree of 1, and 6 to 18 carbon atoms in a fatty acid; polymonoglycerol fatty acid esters having a glycerin polymerization degree of 2 to 10, and 6 to 18 carbon atoms in a fatty acid; organic acid monoglycerides and the like.

Examples of fatty acids constituting the glycerin fatty acid esters may include, for example, caprylic acid, capric acid, lauric acid, myristic acid, palmitic acid, stearic acid, isostearic acid, oleic acid, linoleic acid, linolenic acid and the like.

Examples of the organic acid monoglycerides may include monoglycerin caprylic acid succinic acid ester, monoglycerin stearic acid citric acid ester, monoglycerin stearic acid acetic acid ester, monoglycerin stearic acid succinic acid ester, monoglycerin stearic acid lactic acid ester, monoglycerin stearic acid diacetyl tartaric acid ester, monoglycerin oleic acid citric acid ester and the like.

In a sorbitan fatty acid ester, fatty acids having 6 to 18 carbon atoms may be bound with one or more hydroxyl groups of sorbitan by esterification. More specifically, examples of the sorbitan fatty acid esters may include sorbitan mono lauric acid ester, sorbitan mono palmitic acid ester, sorbitan mono stearic acid ester, sorbitan mono oleic acid ester and the like.

A propylene glycol fatty acid ester may be a monoester or diester in which fatty acids having 6 to 18 carbon atoms are bound with propylene glycol by esterification. Examples of the fatty acid constituting the propylene glycol fatty acid esters may include caprylic acid, capric acid, lauric acid, myristic acid, palmitic acid, stearic acid, isostearic acid, oleic acid, linoleic acid, linolenic acid and the like.

The sucrose fatty acid esters may be prepared from one or more hydroxyl groups of sucrose bound with fatty acids having 6 to 22 carbon atoms by esterification, and examples of the sucrose fatty acid esters may include sucrose lauric acid ester, sucrose myristic acid ester, sucrose palmitic acid ester, sucrose stearic acid ester, sucrose oleic acid ester, sucrose behenic acid ester, sucrose erucic acid ester and the like.

Examples of the lecithins may include all types of lecithins extracted from plants such as soybeans, corn, peanuts, rapeseed, barley and the like; egg yolk; animals such as, cows and the like; and microorganisms such as *Escherichia coli* and the like, and may include glycerolecithins such as phosphatidic acid, phosphatidylglycerin, phosphatidylionsitol, phosphatidylethanolamine, phosphatidylmethylethanolamine, phosphatidylcholine, phosphatidylserine, bisphosphatidic acid, diphosphatidylglycerin and the like; and sphingolecithins such as sphingomyelin and the like. The lecithins may also be hydrogenated lecithin, enzymatically hydrolyzed lecithin, enzymatically hydrolyzed hydrogenated lecithin, hydroxylated lecithin or the like.

Examples of saponins may include enju saponin, quillaja saponin, purified soybean saponin, yucca saponin and the like.

The amount of the emulsifier added is preferably 0.01 to 1% by mass, and more preferably 0.01 to 0.1% by mass based on the yeast cells (wet mass). Also, in the specification, the wet mass refers to the mass of yeast cells with a liquid (dispersion medium).

In one embodiment, the present invention also provides yeast cells reacted with a protease and/or cellulase.

[Quality Improving Material for Food]

In one embodiment, the present invention provides a quality improving material for food containing yeast cells in which the taste is improved according to the method of improving the taste described above, as an active ingredient.

In one embodiment, the present invention also provides yeast cells, which are reacted with a protease and/or cellulose, and mixed with an emulsifier.

In addition, the yeast cells in which the taste is improved according to the method of improving the taste described above are reduced in an undesirable taste (a bitter, astringent, acrid taste or the like) or undesirable smell, which is the characteristic of the yeast cells such as a yeast extract residue or the like. However, since chemicals contained in the yeast cells are very diverse, it is difficult to specify a material causing such an undesirable taste or smell. Moreover, due to the difficulty in specification of such a material, it is also difficult to determine whether the taste of the yeast cells is improved according to the content of the substance.

The quality improving material for food according to the embodiment may contain other ingredients, as long as it contains the yeast cells in which the taste is improved according to the method of improving the taste described above as an active ingredient. Ingredients excluding the yeast cells with improved taste, which are contained in the quality improving material for food, may include, for example, flavoring agents, seasonings, pH-adjusting agents and the like.

Here, the phrase "contained as an active ingredient" means that the yeast cells in which the taste is improved according to the above-described method of improving the taste are contained at an amount that can exhibit a desirable effect of the present invention, for example, preferably at 50% by mass or more, more preferably at 70% by mass or more, and further more preferably at 90% by mass or more, based on the quality improving material for food, but the present invention is not limited thereto. Since the taste of the quality improving material for food of the embodiment is improved, it can be added to foods.

In addition, as will be described below, due to good water-retaining ability and oil-retaining ability, the quality improving material for food of the embodiment may enhance water retention and oil retention when being added to foods, thereby improving food quality. Moreover, as will be described below, the addition of the quality improving material for food may result in a food quality-improving effect, for example, enhancement in softness of lean meat of meat or seafood, juiciness of the lean meat, or crispness of the crust of deep-fried food such as karaage, tempura, croquettes or the like.

The quality improving material for food of the embodiment may contain proteins at 25% by mass or more, β-glucans at 10% by mass or more, and dietary fiber at 25% by mass or more.

The protein content is preferably 40% by mass or more, more preferably 50% by mass or more, and further more preferably 60% by mass or more.

It is known that the β-glucans have an effect of improving an immune function or an antitumor effect, and the dietary fiber has a constipation-improving effect, an effect of activating gastrointestinal motility, a cholesterol-reducing effect, an effect of suppressing an increase in blood pressure, an effect of improving an immune function, and the like.

Thus, the quality improving material for food of the embodiment has an effect of increasing the food quality since it is highly nutritious and has high functionality.

[Powder Mixture]

In one embodiment, the present invention provides a powder mixture containing the above-described quality improving material for food as an active ingredient.

In the specification, the powder mixture means a powdery composition for coating foods in cooking, for example, karaage, tempura or the like, and may include, for example, dusting powder, karaage powder, tempura powder, bread crumb powder and the like. The powder mixture may also be used by being contained in batter, breading or the like. In addition to the above-described quality improved material of food, the powder mixture may also include, for example, wheat flour (cake flour), potato starch, starch, processed starch, baking powder, baker's yeast and the like.

In examples as will be described below, karaage and tempura cooked using the powder mixture of the embodiment were enhanced in juiciness of lean meat. Also, karaage, tempura and croquettes were enhanced in crispness of a crust. Therefore, the powder mixture of the embodiment is able to improve the food quality. The above-described quality improving material for food may also be a quality improving material for food for the powder mixture.

While not being bound by a particular theory, according to an action mechanism for enhancing the juiciness of lean meat and the crispness of a crust, for example, by the adsorption of juice released from the meat to all over the yeast cells, it is difficult for meat to dry out from its surface, and thus it can be considered that this is why the lean meat is juicy. It is also considered that, since release of the meat juice into the crust is suppressed, the crispness of the crust is enhanced. In an example as will be described below, it may be considered that, since water and oil released from lean meat or a crust is trapped by the yeast cells, fried foods are prepared crisp. Alternatively, it can be considered that the water and oil are adsorbed to the entire surface of the yeast cells, and thus fried foods are prepared crisp. In addition, it is considered that, as oil released from a crust itself is also adsorbed to the entire surface of the yeast cells, a situation in which fried foods become soggy due to spread of the oil throughout the crust is prevented, resulting in a contribution to the enhancement of the crispness of the crust.

[Batter]

In one embodiment, the present invention provides batter containing the above-described quality improving material for food as an active ingredient.

In the specification, the batter refers to a liquid or semi-liquid composition for covering food in cooking of croquettes, fried foods or the like. The batter may include, for example, wheat flour (cake flour), egg white powder, eggs, milk, butter, water and the like, in addition to the above-described quality improving material for food. Also, the batter may contain a thickening agent alone or in combination thereof in order to adjust or stabilize viscosity. Examples of the thickening agents may include starch, processed starch, guar gum, xanthan gum, cellulose and the like.

In an example as will be described below, croquettes cooked using the batter of the embodiment were enhanced in crispness of a crust. Therefore, according to the batter of the embodiment, food quality may be improved.

[Fried Food]

In one embodiment, the present invention provides fried food containing the above-described quality improving material for food. The fried food of the embodiment may be cooked using the powder mixture or batter described above. Also, the fried food of the embodiment may be frozen fried food.

In an example as will be described below, the fried food such as karaage, tempura, croquettes, pork cutlets, fried marlin or the like, which contains the above-described food quality improving material for food, is enhanced in crispness of a crust, juiciness of lean meat, softness of the lean meat, texture and the like.

[Softener for Meat or Seafood]

In one embodiment, the present invention provides a softener for meat or seafood, which contains the above-described quality improving material for food as an active ingredient.

The softener of the embodiment may be contained in a seasoning liquid such as a pickling liquid, and then injected into meat or seafood. Alternatively, the meat or seafood may be marinated with a marinade containing the softener of the embodiment. Alternatively, the softener of the embodiment may be contained in food such as a hamburger or the like.

In an example as will be described below, the softness of lean meat of meat or seafood may be enhanced using the softener of the embodiment. More specifically, the softness of lean meat was enhanced by marinating salad chicken (steamed, marinated chicken for a salad topping), beef, chicken, squid, marlin or the like with a marinade containing the softener of the embodiment. In addition, ham or a pork cutlet was capable of being enhanced in softness of lean meat by injecting a pickling liquid containing the softener of the embodiment into pork loin. In addition, the softness of lean meat was enhanced by adding the softener of the embodiment to a hamburger patty. Therefore, the softener of the embodiment is able to soften lean meat of the meat or seafood.

While not being bound by a particular theory, the inventors have assumed that the effect of softening meat or seafood by the softener of the embodiment may be caused by yeast cells still having a three-dimensional structure as a cell, and thus the structure is hardly destroyed even by heating. More specifically, it seems that toughening of lean meat caused by contraction of muscle fibers is prevented because the yeast cells are added between the muscle fibers of the lean meat while having the three-dimensional structure as a cell. In addition, it seems that the yeast cells are smaller than red blood cells in size, have a major axis of approximately 4 to 6 μm, and may be easily injected into tissue such as lean meat or the like, like components of the lymphatic fluid in the body. In addition, it is considered that the adsorption of water or the like to the inside or surface of a yeast extract residue also contributes to the softening effect.

[Method of Softening Meat or Seafood]

In one embodiment, the present invention provides a method of softening meat or seafood, which includes contacting meat or seafood with the above-described quality improving material for food (softener). The softening method of the embodiment may also be a method of preparing meat or seafood enhanced in softness of lean meat, which includes contacting meat or seafood with the above-described quality improving material for food.

Here, the contacting with the quality improving material for food may be injection of the quality improving material for food which has been previously contained in a seasoning liquid such as a pickling liquid or the like into the meat or seafood. Alternatively, the meat or seafood may be marinated with a marinade containing the quality improving material for food. Alternatively, the quality improving material for food may be contained in a material for food such as a hamburger patty or the like. In an example as will be described below, the meat or seafood may be softened by such a method.

[Method for Preventing Syneresis or Oil Separation of Processed Food]

In one embodiment, the present invention provides a method for preventing syneresis or oil separation of processed food (or enhanced in water or oil retention), the method including contacting a food material with the above-described quality improving material for food.

Here, the contacting with the quality improving material for food may also be coating a food material such as meat, seafood or the like with karaage powder, dusting powder, breading, tempura powder, batter or the like, which contains the quality improving material for food. Alternatively, the quality improving material for food may be added to a seasoning liquid such as a pickling liquid or the like, and then injected into the food material. Alternatively, the food material may be marinated with a marinade containing the food quality improving material for food. Alternatively, the food quality improving material for food may be added to the food material such as tuna, a hamburger patty or the like.

In an example as will be described below, the food prepared by the preparation method according to the embodiment is prevented syneresis or oil separation. For this reason, the food may obtain effects of enhancement in yield, enhancement in juiciness of lean meat and the like. The food may also obtain effects of preventing a soggy crust caused by oil separated from the crust of karaage, tempura or the like over time and then floated on the surface of the food, or preventing a soggy crust caused by water separated from a material (lean meat) for karaage and then permeated into the crust.

EXAMPLES

Hereinafter, although the present invention will be described with reference to experimental examples, the present invention is not limited to the following experimental examples.

Experimental Example 1

(Investigation of Enzymes)

Reduction in an undesirable smell was investigated with the reaction of yeast cells with various enzymes. As yeast cells, a yeast extract residue generated by extracting a yeast extract from baker's yeast cultivated by a conventional method through hydrothermal extraction was used.

First, the yeast cells were sterilized at 85 to 90° C. for 30 minutes. Subsequently, after cooling, the yeast cells were treated with various enzymes shown in Table 1 at amounts shown in Table 1 to allow a reaction at 50° C. for 6 hours. Subsequently, the yeast cells were treated at 80° C. for 20 minutes to deactivate the enzymes. Subsequently, after cooling, the yeast cells were washed with water three times.

Sensory evaluation was performed with four grades A to D, with respect to the reduction in an undesirable smell of the resulting yeast cells. "A" represents a great decrease in an undesirable smell, and "D" represents that a decrease in an undesirable smell was hardly observed.

Results are shown in Table 1. It was shown that the effect of reducing an undesirable smell is highly exhibited using a protease-type enzyme. It was also confirmed that an endo-type protease has a higher tendency to reduce an undesirable smell than an exo-type protease.

TABLE 1

| Type of enzyme | Origin of enzyme | Amount of enzyme added [unit/ 1 g yeast cells (solid content)] | Effect of reducing undesirable smell |
|---|---|---|---|
| Endo-type and exo-type protease | *Rhizopus niveus* | 300 to 400 | C |
| Endo-type protease | *Bacillus amyloliquefaciens* | 700 | A |
| Endo-type protease | *Bacillus lichenifonnis* | 800 | A |
| Endo-type and exo-type protease | *Aspergillus oryzae* | 400 | B |
| Endo-type and exo-type protease | *Aspergillus oryzae* | 500 | B |
| Endo-type and exo-type protease | *Aspergillus melleus* | 3000 | B |
| Endo-type and exo-type protease | *Aspergillus oryzae* | 14 | B |
| Laccase | Bacteria of the genus *Trametes* | 1080 | D |
| Glycooxidase | *Aspergillus niger* | 15 | C |
| β-glycosidase | *Penicillium* multicolor | 0.8 | C |
| Endo-type protease | *Bacillus stearothermophilus* | 900 | B |
| Lipase | *Rhizopus oryzae* | 4.2 | D |
| Endo-type protease | *Bacillus amyloliquefaciens* | 210 | B |
| Laccase | Bacteria of the genus *Trametes* | 210 | D |
| Glycooxidase | *Aspergillus niger* | 210 | D |
| Cellulase | — | 210 | C |
| No addition of enzyme | — | — | D |

Experimental Example 2

(Investigation of Yeast Types)

The reduction in an undesirable smell was investigated by reacting cells of torula yeast, baker's yeast and beer yeast as yeast cells with a protease.

As torula yeast cells, a yeast extract residue generated by extracting a yeast extract from torula yeast through enzymatic degradation was used. As baker's yeast cells, a yeast extract residue generated by extracting a yeast extract from baker's yeast by a hydrothermal treatment method was used. Beer yeast was prepared in a solution in which processed powder of yeast after beer brewing, which is commercially available, was suspended in water at a concentration of 20 w/v % before use.

First, each type of the yeast cells described above was sterilized at 90° C. for 30 minutes. Subsequently, after cooling, the pH was adjusted to 7.0. Subsequently, a *Bacillus amyloliquefaciens*-derived endo-type protease was added at 210 units per 1 g of the yeast cells (solid content) to allow a reaction at 50° C. for 6 hours. Subsequently, the yeast cells were treated at 80° C. for 20 minutes to deactivate the enzyme. Subsequently, after cooling, the yeast cells were washed with water and then dried.

The resulting yeast cells were suspended at a concentration of 2 w/v %, and sensory evaluation was performed with four grades A to D with respect to the reduction in an undesirable smell of the yeast cells. "A" represents a great decrease in an undesirable smell, and "D" represents that a decrease in an undesirable smell was hardly observed.

Results are shown in Table 2. It was confirmed that, even when beer yeast was used as a food ingredient, a certain effect was exhibited, but when torula yeast and baker's yeast were used as food ingredients, the effect of reducing an undesirable smell was highly exhibited.

TABLE 2

|  | Torula yeast | Baker's yeast | Beer yeast |
|---|---|---|---|
| Effect of reducing undesirable smell | A | A | C |

Experimental Example 3

(Investigation of Emulsifier 1)

The reduction in an undesirable taste was investigated by reacting yeast cells with a protease and adding various emulsifiers. As yeast cells, a yeast extract residue generated by extracting a yeast extract from baker's yeast by a hydrothermal extraction method was used.

First, various emulsifiers shown in Table 3 were added to the yeast cells at 0.05% by mass, based on the yeast cells (wet mass). Subsequently, the yeast cells were sterilized at 90° C. for 30 minutes. Subsequently, after cooling, the pH was adjusted to 7.0. Subsequently, a *Bacillus amyloliquefaciens*-derived endo-type protease was added at 210 units per 1 g of the yeast cells (solid content) to allow a reaction at 50° C. for 6 hours. Subsequently, the yeast cells were treated at 80° C. for 20 minutes to deactivate the enzyme.

Subsequently, the yeast cells were cooled, washed with water, and then dried.

The resulting yeast cells were suspended in water at a concentration of 2 w/v %, and sensory evaluation was performed with three grades A to C with respect to the reduction in an undesirable taste (bitter, astringent or acrid taste) of yeast cells. "A" represents a great decrease in an undesirable taste, and "C" represents that a decrease in an undesirable taste was hardly observed.

Results are shown in Table 3. It was confirmed that an undesirable taste such as a bitter, astringent, acrid taste or the like tends to be further reduced by adding the emulsifier to the yeast cells, compared to the yeast cells which were reacted only with a protease.

TABLE 3

| Type of emulsifier | HLB value | Type of glycerin | Effect of reducing undesirable taste |
|---|---|---|---|
| Sugar ester | 15.0 | — | C |
| Glycerin fatty acid ester | 2.8 | Monoglyceride | A |
| Glycerin fatty acid ester | 4.1 | Monoglyceride | A |
| Glycerin fatty acid ester | 4.6 | Decaglycerin | A |
| Glycerin fatty acid ester | 7.0 | Polyglycerin | A |
| Glycerin fatty acid ester | 14.0 | Decaglycerin | B |
| Enzymatically hydrolyzed lecithin(1) | — | — | B |
| Enzymatically hydrolyzed lecithin(2) | — | — | B |
| Saponin | — | — | B |
| No addition of emulsifier | — | — | C |

Experimental Example 4

(Investigation of Emulsifier 2)

The effect of adding an emulsifier was investigated by changing the time for adding the emulsifier to yeast cells from the addition timing in Experimental Example 3. As yeast cells, a yeast extract residue generated by extracting a yeast extract from baker's yeast cultivated by a conventional method through hydrothermal extraction was used. First, the yeast cells were sterilized at 90° C. for 30 minutes. Subsequently, after cooling, the pH was adjusted to 7.0. Subsequently, a *Bacillus amyloliquefaciens*-derived endo-type protease was added at 210 units per 1 g of the yeast cells (solid content) to allow a reaction at 50° C. for 6 hours. Subsequently, various emulsifiers shown in Table 4 were added to the yeast cells at 0.05% by mass, based on the yeast cells (wet mass). Subsequently, the yeast cells were treated at 80° C. for 20 minutes to deactivate the enzyme. Subsequently, after cooling, the yeast cells were washed with water, and then dried.

The resulting yeast cells were suspended in water at a concentration of 2 w/v %, and sensory evaluation was performed with three grades A to C with respect to the reduction in an undesirable taste (bitter, astringent, acrid taste) of the yeast. "A" represents a great decrease in an undesirable taste, and "C" represents that a decrease in an undesirable taste was hardly observed.

Results are shown in Table 4. It was confirmed that an undesirable taste such as a bitter, astringent, acrid taste or the like tends to be degraded by adding the emulsifier, regardless of the time for adding the emulsifier.

TABLE 4

| Type of emulsifier | HLB value | Type of glycerin | Effect of degrading undesirable taste |
|---|---|---|---|
| Sugar ester | 15.0 | — | C |
| Glycerin ester of fatty acids | 4.1 | Monoglyceride | A |

Experimental Example 5

(Preparation of Yeast Cells with Improved Taste 1)

Preparation Example 1

Yeast cells in which the taste was improved were prepared by reacting yeast cells with a protease. As the yeast cells, a yeast extract residue generated by extracting a yeast extract from baker's yeast through hydrothermal extraction was used. First, the yeast cells were sterilized at 85° C. for 30 minutes. Subsequently, after cooling, a *Bacillus amyloliquefaciens*-derived endo-type protease was added at 245 units per 1 g of to the yeast cells (solid content) to allow a reaction at 50° C. for 6 hours. Subsequently, the yeast cells were treated at 80° C. for 20 minutes to deactivate the enzyme. Subsequently, after cooling, the yeast cells were washed with water three times, and dried using a drum dryer. Subsequently, the dried product was crushed into powder with a size of 50 mesh pass, thereby obtaining a sample (yeast cells) of Preparation Example 1.

Preparation Example 2

Deodorized yeast cells were prepared according to a conventional method. As yeast cells, a yeast extract residue generated by extracting a yeast extract from baker's yeast through hydrothermal extraction was used. First, the yeast cells were diluted with water to double the volume. Subsequently, sodium hydroxide was added to the yeast cells at 0.4 w/v %. Subsequently, the yeast cells were sterilized at 85° C. for 30 minutes. Subsequently, the pH was adjusted to 7.0 with citric acid. Subsequently, the yeast cells were washed with three times, and dried using a drum dryer. Subsequently, the resulting dried product was crushed into powder with a size of 50 mesh pass, thereby obtaining a sample of Preparation Example 2.

Preparation Example 3

As a control, yeast cells subjected to pH adjustment were prepared. As yeast cells, a yeast extract residue generated by extracting a yeast extract from baker's yeast through hydrothermal extraction was used.

First, the yeast cells were sterilized at 85° C. for 30 minutes. Subsequently, the pH was adjusted to 7.0 with citric acid. Subsequently, the yeast cells were dried using a drum dryer. Subsequently, the resulting dried product was crushed into powder with a size of 50 mesh pass, thereby obtaining a sample of Preparation Example 3.

Experimental Example 6

(Evaluation of Yeast Cells)

Properties (ingredients, water retention rate, oil retention rate, settling volume in water, bulk density) of the samples of Preparation Examples 1 to 3 prepared in Experimental Example 5 were analyzed.

(Ingredient Analysis)

Ingredient analyses were carried out on the yeast cells of Preparation Examples 1 to 3. Analysis results are shown in Table 5. A water content was measured according to an atmospheric pressure dry gravimetric method under dry conditions at 105° C. for 3 hours. A solid content was calculated by subtracting the water content (%) from 100 (%). Salinity was measured by a potentiometric titration method. The total nitrogen content was measured by the Kjeldahl method. A protein content was calculated by multiplying the total nitrogen content by 6.25. The β-glucan content was measured by an enzymatic method. A dietary fiber content was determined by an enzyme-gravimetric method.

TABLE 5

| Analysis items | Unit | Preparation Example 1 | Preparation Example 2 | Preparation Example 3 |
|---|---|---|---|---|
| Water content | mass % | 4.81 | 4.80 | 5.43 |
| Solid content | mass % | 95.19 | 95.20 | 94.57 |
| pH (2 w/v % solution) | — | 8.78 | 7.86 | 7.67 |
| Salinity | mass % | 0.04 | 0.05 | 1.36 |
| Total nitrogen content | mass %/solid content | 9.85 | 8.64 | 10.05 |
| Protein content (F = 6.25) | mass %/solid content | 61.56 | 53.99 | 62.78 |
| Total sulfur content | mass %/solid content | 22.14 | 17.71 | 20.55 |
| Dietary fiber content | g/100 g | 27.9 | — | 23.6 |
| Cellulose content | g/100 g | 0.6 | — | 0.7 |
| β-glucan content | mass %/solid content | 12.82 | 17.10 | 10.63 |
| β-glucan content | g/100 g | 13.1 | — | 10.2 |
| β-glucan content/Total sulfur content | mass % | 57.90 | 96.53 | 51.74 |
| Total amino acids | mg/100 g | 53314 | 48526 | 45443 |
| Free amino acids | mg/100 g | 108 | 126 | 595 |

(Measurement of Water Retention Rate)

The water retention rates of the samples of Preparation Examples 1 to 3 were measured as follows. First, 100 mL of hot water was added to 5 g of each sample. Subsequently, the sample was suspended and allowed to stand for 30 minutes. Subsequently, the resulting suspension was centrifuged at 1000×g for 15 minutes, and then the supernatant was removed. Subsequently, the resulting precipitate was subjected to the measurement of a wet mass. Subsequently, the resulting precipitate was dried at 105° C. for 4 hours, and then its dry mass was measured. Subsequently, the water retention rate was calculated by the following formula. As a control, the water retention rate of dietary fiber (trade name "Beet Fiber," produced by Nippon Beet Sugar Producing Co., Ltd.) was also measured. The measurement results are shown in Table 6.

Water retention rate (%)=Wet mass of precipitate (g)/Dry mass of precipitate (g)×100

(Measurement of Oil Retention Rate)

The oil retention rates of the yeast cells of Preparation Examples 1 to 3 were measured as follows. First, 40 g of salad oil was added to 3 g of each sample, and then suspended using a vortex mixer. Subsequently, the resulting suspension was centrifuged at 1000×g for 15 minutes, and then the supernatant was removed. Subsequently, a wet mass of the resulting precipitate was measured.

Subsequently, oil retention rates were calculated according to the following formula. As a control, the oil retention rate of a commercially-available dietary fiber material (trade name "Beet Fiber," produced by Nippon Beet Sugar Producing Co., Ltd.) was also measured. The measurement results are shown in Table 6.

Oil retention rate (%)=Wet mass of precipitate (g)/Mass of sample (g)×100

(Measurement of Settling Volume in Water (Swellability))

The settling volumes in water of the samples of Preparation Examples 1 to 3 were measured as follows. First, 1 g of each sample was weighed in a 50 mL graduated cylinder, suspended by adding water, and diluted to a final volume of 50 mL. Subsequently, after being allowed to stand for 1 hour, a settling volume in water was measured. As a control, the settling volume in water of dietary fiber (trade name "Beet Fiber," Nippon Beet Sugar Producing Co., Ltd.) was also measured. The measurement results are shown in Table 6.

(Measurement of Bulk Density)

The bulk densities of the samples of Preparation Examples 1 to 3 were measured as follows. First, 20 g of each sample was weighed in a 100 mL graduated cylinder. Subsequently, the bottom of the graduated cylinder was tapped on a desk three times. Subsequently, a graduation of the graduated cylinder was read, and therefore the volume of the sample was determined. The measurement results are shown in Table 5.

TABLE 6

| | Preparation Example 1 | Preparation Example 2 | Preparation Example 3 | Dietary fiber |
|---|---|---|---|---|
| Water retention rate (%) | 467 | 925 | 565 | 795 |
| Oil retention rate (%) | 335 | 410 | 283 | 250 |
| Settling volume in water (cm$^3$/g) | 6 | 12 | 3.5 | 7.5 |
| Bulk density (g/cm$^3$) | 0.33 | 0.26 | 0.40 | — |

Experimental Example 7

(Preparation of Yeast Cells with Improved Taste 2)

Preparation Example 4

A sample of Preparation Example 4 was obtained in the same manner as described in Preparation Example 1, except that a *Bacillus amyloliquefaciens*-derived endo-type protease was added at an amount of 280 units per 1 g of yeast cells (solid content).

Preparation Example 5

To obtain the effect of improving the taste, yeast cells supplemented with vitamin C were prepared. As yeast cells, a yeast extract residue generated by extracting a yeast extract from baker's yeast through hydrothermal extraction was used. First, the yeast cells were sterilized at 85° C. for 30 minutes. Subsequently, after cooling, 0.25 w/v % of vitamin C was added. Subsequently, the yeast cells were dried using a drum dryer. Subsequently, the resulting dried product was crushed into powder with a size of 50 mesh pass, thereby obtaining a sample of Preparation Example 5.

Preparation Example 6

To obtain the effect of improving the taste, yeast cells supplemented with citric acid were prepared. As yeast cells, a yeast extract residue generated by extracting a yeast extract from baker's yeast through hydrothermal extraction was used. First, the yeast cells were sterilized at 85° C. for 30 minutes. Subsequently, after cooling, 0.25 w/v % of citric acid was added. Subsequently, the yeast cells were dried using a drum dryer. Subsequently, the yeast cells were crushed into powder with a size of 50 mesh pass, thereby obtaining a sample of Preparation Example 6.

Preparation Example 7

To obtain the effect of improving the taste, yeast cells were prepared by bubbling treatment using air. As yeast cells, a yeast extract residue generated by extracting a yeast extract from baker's yeast through hydrothermal extraction was used. First, the yeast cells were sterilized at 85° C. for 30 minutes. Subsequently, after cooling, the bubbling treatment was performed through aeration. Subsequently, the yeast cells were dried using a drum dryer. Subsequently, the yeast cells were crushed into powder with a size of 50 mesh pass, thereby obtaining a sample of Preparation Example 7.

Experimental Example 8

(Evaluation of Yeast Cells)

Sensory evaluation for the taste (smell and taste) of yeast cells was performed by blind tests with respect to 6 testers with suspensions in which the samples of Preparation Examples 1, 2, 4 to 7 were suspended in water at a concentration of 2 w/v %. Specifically, the sample of the yeast cells of each Preparation Example was ranked in descending orders of smell, taste and total evaluation of both smell and taste. Subsequently, the ranks were converted into scores as follows: First place: +3 points, Second place: +2 points, Third place: +1 point, Fourth place: −1 point, Fifth place: −2 points, and Sixth place: −3 points.

Results are shown in Table 7. In the total evaluation, the yeast cells of Preparation Example 1 (protease treated) and Preparation Example 4 (protease treated) were highly ranked. In terms of smell, the yeast cells of Preparation Example 4 (protease treated) and Preparation Example 6 (citric acid treated) were equally ranked. In terms of taste, the yeast cells of Preparation Example 1 (protease treated) and Preparation Example 4 (protease treated) were highly ranked.

TABLE 7

|  | Smell | Taste | Total |
|---|---|---|---|
| Preparation Example 1 (protease treated) | −6.5 | 3 | 3 |
| Preparation Example 4 (protease treated) | 5.5 | 3.5 | 2 |
| Preparation Example 5 (vitamin C added) | −2.5 | −4.5 | 1 |
| Preparation Example 7 (bubbling treated) | 1.5 | −1 | 0.5 |

TABLE 7-continued

|  | Smell | Taste | Total |
|---|---|---|---|
| Preparation Example 6 (citric acid added) | 4.5 | −3 | −2.5 |
| Preparation Example 2 (sodium hydroxide treated) | −5.5 | −4 | −6.5 |

Experimental Example 9

(Measurement of Water Retention Rate)

Water retention rates were measured with respect to the samples of Preparation Examples 1, 2, 4 to 7, commercially-available samples that are listed below, and a sample prepared by drying a yeast extract residue generated by extracting a yeast extract from baker's yeast through hydrothermal extraction using a drum dryer (hereinafter, may be referred to as "yeast extract residue" in some cases) in the same manner as described in Experimental Example 6. Results are shown in Table 8.

Processed α-starch
  Trade name "Pine soft S" (produced by Matsutani Chemical Industry Co., Ltd.)
  Trade name "Jelcall AH-F"(produced by J-Oil Mills, Inc.)
Dietary fiber (pectin, hemicellulose, cellulose or the like)
  Trade name "Beet Fiber" (Nippon Beet Sugar Producing Co., Ltd.)
  Trade name "NEW Beet Fiber" (produced by Nippon Beet Sugar Producing Co., Ltd.)
Crystalline Cellulose
  Trade name "Ceolus DX-2" (produced by Asahi Kasei Chemicals Corporation)
Soybean Protein
  Trade name "FUJIPRO FR" (produced by Fuji Oil Co., Ltd.)
Starch
Wheat flour
Rice flour
Others
Curdrun
CM cellulose
Cornstarch

TABLE 8

| Sample | Sample amount (g) | Wet mass of precipitate (g) | Water content (%) | Solid content (%) | Dry mass of precipitate (g) | Water retention rate (%) |
|---|---|---|---|---|---|---|
| Yeast extract residue | 5.0 | 23.43 | 82.3 | 17.7 | 4.1 | 565.3 |
| Preparation Example 1 | 5.0 | 22.25 | 78.6 | 21.4 | 4.8 | 467.1 |
| Preparation Example 2 | 5.0 | 38.55 | 89.2 | 10.8 | 4.2 | 925.1 |
| Preparation Example 4 | 5.0 | 22.82 | 79.0 | 21.0 | 4.8 | 476.2 |
| Preparation Example 5 | 5.0 | 18.57 | 76.3 | 23.7 | 4.4 | 422.1 |
| Preparation Example 6 | 5.0 | 22.70 | 79.6 | 20.4 | 4.6 | 490.0 |
| Preparation Example 7 | 5.0 | 22.79 | 79.8 | 20.2 | 4.6 | 495.5 |
| Pine soft S | 5.0 | 33.76 | 87.4 | 12.6 | 4.3 | 793.7 |
| Jelcall AH-F | 5.0 | 27.72 | 84.84 | 15.2 | 4.2 | 659.6 |
| Beet Fiber | 5.0 | 32.85 | 87.4 | 12.6 | 4.1 | 794.9 |
| NEW Beet Fiber | 5.0 | 30.14 | 86.2 | 13.8 | 4.1 | 726.7 |
| Ceolus DX-2 | 5.0 | 14.79 | 88.2 | 11.9 | 1.8 | 843.9 |
| Fuji Pro FR | 5.0 | 44.57 | 93.2 | 6.8 | 3.0 | 1462.0 |
| Wheat flour | 5.0 | 32.46 | 87.5 | 12.5 | 4.1 | 800.0 |
| Rice powder | 5.0 | 36.88 | 87.9 | 12.1 | 4.5 | 825.1 |

TABLE 8-continued

| Sample | Sample amount (g) | Wet mass of precipitate (g) | Water content (%) | Solid content (%) | Dry mass of precipitate (g) | Water retention rate (%) |
|---|---|---|---|---|---|---|
| Curdrun | 5.0 | 46.24 | 91.5 | 8.6 | 4.0 | 1169.6 |
| CM Cellulose | 5.0 | 28.13 | 91.1 | 8.9 | 2.5 | 1126.1 |
| Cornstarch | 5.0 | 42.95 | 86.5 | 13.5 | 5.8 | 741.3 |

Experimental Example 10

(Measurement of Oil Retention Rate)

Oil retention rates were measured with respect to the samples of Preparation Examples 1, 2, 4 to 7, the commercially-available samples, which were the same as used in Experimental Example 9, and a sample prepared by drying a yeast extract residue generated by extracting a yeast extract from baker's yeast through hydrothermal extraction using a drum dryer (hereinafter, may be referred to as "yeast extract residue" in some cases) in the same manner as described in Experimental Example 6.

Results are shown in Table 9. The samples of Preparation Examples 1, 2, 4 to 7 showed the oil retention rates, which were the same as or higher than the commercially available samples.

TABLE 9

| Sample | Sample amount (g) | Wet mass of precipitate (g) | Oil retention rate (%) |
|---|---|---|---|
| Yeast extract residue | 3.0 | 8.49 | 283.0 |
| Preparation Example 1 | 3.0 | 10.06 | 335.3 |
| Preparation Example 2 | 3.0 | 12.31 | 410.3 |
| Preparation Example 4 | 3.0 | 8.04 | 268.0 |
| Preparation Example 5 | 3.0 | 8.32 | 277.3 |
| Preparation Example 6 | 3.0 | 6.25 | 208.3 |
| Preparation Example 7 | 3.0 | 7.3 | 243.3 |
| Pine soft S | 3.0 | 6.14 | 204.7 |
| Jelcall AH-F | 3.0 | 6.7 | 223.3 |
| Beet Fiber | 3.0 | 7.5 | 250.0 |
| NEW Beet Fiber | 3.0 | 8.52 | 284.0 |
| Ceolus DX-2 | 3.0 | 5.93 | 197.7 |
| Fuji Pro FR | 3.0 | 6.72 | 224.0 |
| Wheat flour | 3.0 | 5.42 | 180.7 |
| Rice flour | 3.0 | 6.28 | 209.3 |
| Curdrun | 3.0 | 6.49 | 216.3 |
| CM Cellulose | 3.0 | 18.89 | 629.7 |
| Cornstarch | 3.0 | 5.22 | 174.0 |

Experimental Example 11

(Measurement of Water/Oil Adsorption Rate)

Water/oil adsorption rates were measured with respect to the samples of Preparation Examples 1, 2, 4 to 7, the commercially-available samples, which were the same as used in Experimental Example 9, and a sample prepared by drying a yeast extract residue generated by extracting a yeast extract from baker's yeast through hydrothermal extraction using a drum dryer (hereinafter, may be referred to as "yeast extract residue" in some cases). Specifically, first, 20 g of distilled water was added to 3 g of each sample, and then gently suspended. Subsequently, 20 g of salad oil was added, and then suspended using a vortex mixer. Subsequently, each sample was centrifuged at 1000×g for 15 minutes, and then the supernatant was removed.

Subsequently, a wet mass of the resulting precipitate was measured.

Subsequently, water/oil adsorption rates were calculated by the following formula.

Water/oil adsorption rate (%)=Wet mass of precipitate (g)/Mass of sample (g)×100

Measurement results are shown in Table 10. It was confirmed that the samples of Preparation Examples 1, 2, 4 to 7 tended to exhibit high performance of retaining both water and oil.

TABLE 10

| Sample | Sample amount (g) | Wet mass of precipitate (g) | Water in precipitate (%) | Water in precipitate (g) | Oil in precipitate (%) | Oil in precipitate (g) | Water/Oil adsorption rate (%) |
|---|---|---|---|---|---|---|---|
| Yeast extract residue | 3.0 | 11.22 | 68.5 | 7.7 | 4.8 | 0.5 | 374.0 |
| Preparation Example 1 | 3.0 | 11.94 | 67.8 | 8.1 | 7.1 | 0.8 | 398.0 |
| Preparation Example 2 | 3.0 | 14.79 | 73.0 | 10.8 | 6.7 | 1.0 | 493.0 |
| Preparation Example 4 | 3.0 | 11.83 | 69.6 | 8.2 | 5.0 | 0.6 | 394.3 |
| Preparation Example 5 | 3.0 | 12.97 | 67.1 | 8.7 | 9.8 | 1.3 | 432.3 |
| Preparation Example 6 | 3.0 | 11.0 | 69.7 | 7.7 | 3.1 | 0.3 | 366.7 |
| Preparation Example 7 | 3.0 | 10.79 | 70.2 | 7.6 | 2.0 | 0.2 | 359.7 |

TABLE 10-continued

| Sample | Sample amount (g) | Wet mass of precipitate (g) | Water in precipitate (%) | Water in precipitate (g) | Oil in precipitate (%) | Oil in precipitate (g) | Water/Oil adsorption rate (%) |
|---|---|---|---|---|---|---|---|
| Pine soft S | 3.0 | 16.58 | 81.8 | 13.6 | 0.1 | 0.0 | 552.7 |
| Jelcall AH-F | 3.0 | 11.36 | 72.1 | 8.2 | 1.5 | 0.2 | 378.7 |
| Beet Fiber | 3.0 | 15.77 | 80.5 | 12.7 | 0.5 | 0.1 | 525.7 |
| NEW Beet Fiber | 3.0 | 15.33 | 81.0 | 12.4 | −0.5 | −0.1 | 511.0 |
| Ceolus DX-2 | 3.0 | 12.07 | 80.9 | 9.8 | −5.8 | −0.7 | 402.3 |
| Fuji Pro FR | 3.0 | 38.42 | 53.3 | 20.5 | 38.9 | 14.9 | 1280.7 |
| Wheat flour | 3.0 | 5.39 | 40.2 | 2.2 | 4.1 | 0.2 | 179.7 |
| Rice flour | 3.0 | 6.55 | 42.4 | 2.8 | 11.8 | 0.8 | 218.3 |
| Curdrun | 3.0 | 18.18 | 80.0 | 14.5 | 3.5 | 0.6 | 606.0 |
| CM Cellulose | 3.0 | 15.29 | 77.9 | 11.9 | 2.5 | 0.4 | 509.7 |
| Cornstarch | 3.0 | 5.77 | 39.8 | 2.3 | 8.2 | 0.5 | 192.3 |

Experimental Example 12

(Preparation of Yeast Cells with Improved Taste 3)

Preparation Example 8

Yeast cells with improved taste were prepared using a protease and an emulsifier. As the yeast cells, a yeast extract residue generated by extracting a yeast extract from baker's yeast through hydrothermal extraction was used. First, a glycerin fatty acid ester having a HLB value of 4.1 was added to the yeast cells at 0.05% by mass, based on the yeast cells (wet mass). Subsequently, the yeast cells were sterilized at 90 to 92° C. for 30 minutes. Subsequently, after cooling, the pH was adjusted to 7.0. Subsequently, a *Bacillus amyloliquefaciens*-derived endo-type protease was added at 210 units per 1 g of the yeast cells (solid content), and reacted at 50° C. for 6 hours. Subsequently, the yeast cells were treated at 80° C. for 20 minutes to deactivate the enzyme. Subsequently, after cooling, the yeast cells were washed with water three times, and then dried using a drum dryer. Subsequently, the yeast cells were crushed into powder with a size of 50 mesh pass, thereby obtaining a sample of Preparation Example 8.

Experimental Example 13

(Ingredient Analysis)

Ingredient analysis was performed for the sample of Preparation Example 8. The analysis result is shown in Table 11. A water content was measured according to an atmospheric pressure dry gravimetric method under dry conditions at 105° C. for 3 hours. A solid content was calculated by subtracting the water content (%) from 100(%). Salinity was measured by a potentiometric titration method.

The total nitrogen content was measured according to the Kjeldahl method. The protein content was calculated by multiplying the total nitrogen content by 6.25. The fatty acid content was measured by a Soxhlet extraction method. The ash content was measured by a direct ashing method. The β-glucan content was measured by an enzymatic method. A dietary fiber content was determined by an enzyme-gravimetric method.

TABLE 11

| Analysis item | Unit | Measurement value |
|---|---|---|
| Water content | mass % | 5.19 |
| Solid content | mass % | 94.81 |
| Salinity | mass % | 0.00 |
| Total nitrogen content | mass %/solid content | 8.86 |
| Protein content (F = 6.25) | mass %/solid content | 55.37 |
| Fatty acid content | mass %/solid content | 1.51 |
| Ash content | mass %/solid content | 1.69 |
| β-glucan content | mass %/solid content | 13.81 |
| Dietary fiber content | mass %/solid content | 34.7 |

Experimental Example 14

(Electron Microscopic Observation)

The form of the sample of Preparation Example 8 was observed with an electron microscope. Specifically, the specimen (sample of Preparation Example 8) was adhered to a specimen station of an ion sputtering apparatus (Model No. "E-1010," produced by Hitachi, Ltd.) with a carbon double-sided tape for a scanning electron microscope (Catalog No. "7322," produced by Nisshin EM Co., Ltd.), and discharged for 2 minutes under the conditions of 10 Pa and an ion current of 15 mA for coating. Subsequently, using a scanning electron microscope (Model No. "S-3000 N," produced by Hitachi, Ltd.), the specimen coated under a high vacuum mode and an acceleration voltage of 15 kV was observed. FIG. 1 is an electron micrograph (500× magnification). In FIG. 1, those that look like particles are yeast cells. As a result, it can be seen that the shape of cells still remained in the sample of Preparation Example 8.

Experimental Example 15

(Measurement of Water Retention Rate)

The water retention rate of the sample of Preparation Example 8 was measured. As controls, water retention rates of cellulose powder (trade name "KC Flock," produced by Nippon Paper Chemicals Co., Ltd.), crystalline cellulose (trade name "Ceolus DX-2," produced by Asahi Kasei Chemicals Co., Ltd.), and soy protein (trade name "Fuji Pro FR," Fuji Oil Co., Ltd.) were also measured.

The water retention rates were measured as follows. First, 10 g of a dry sample having a water content of 10% or less was weighed, and 30 g of a paste-type sample having a water content higher than 10% was weighed, and then 100 mL of hot water was added. Subsequently, the sample was allowed to stand for 20 minutes to sufficiently absorb the water, and then cooled to room temperature. Subsequently, the sample was centrifuged at 1000×g for 5 minutes, and then the supernatant was removed. Subsequently, the wet mass of the resulting precipitate was measured. Subsequently, the resulting precipitate was dried at 105° C. for 4 hours, and a dry mass was measured.

Subsequently, the water retention rate was calculated by the following formula. The measurement results are shown in Table 12.

Water retention rate (%)=Wet mass of precipitate (g)/Dry mass of precipitate (g)×100

Experimental Example 16

(Measurement of Oil Retention Rate)

The oil retention rate of the sample of Preparation Example 8 was measured. As controls, oil retention rates of cellulose powder (trade name "KC Flock," produced by Nippon Paper Chemicals Co., Ltd.), crystalline cellulose (trade name "Ceolus DX-2," produced by Asahi Kasei Chemicals Co., Ltd.), and soy protein (trade name "Fuji Pro FR," produced by Fuji Oil Co., Ltd.) were also measured.

The oil retention rates were measured as follows. First, 2.5 g of each sample was weighed. A suitable amount of salad oil was added to the sample, and suspended with a vortex mixer. Subsequently, the sample was centrifuged at 1400×g for 15 minutes, and then the supernatant was removed. Subsequently, the wet mass of the resulting precipitate was measured. Subsequently, an oil retention rate was calculated by the following formula. Measurement results are shown in Table 12.

Oil retention rate (%)=Wet mass of precipitate (g)/Mass of sample (g)×100

TABLE 12

| | Water retention rate (%) | Oil retention rate (%) |
|---|---|---|
| Preparation Example 8 | 540 | 510 |
| KC Flock | 600 | 530 |
| Ceolus DX-2 | 420 | 295 |
| Fuji Pro FR | 540 | 200 |

Experimental Example 17

(Evaluation as Quality Improving Material for Food 1)

The sample of Preparation Example 8 was added as a sample to a hamburger, and the effects on yield, texture and freezing tolerance were evaluated. As a control, cellulose powder (trade name "KC Flock," produced by Nippon Paper Chemicals Co., Ltd.) was used. Also, as a negative control, a hamburger in which neither the sample of Preparation Example 8 nor the cellulose powder was added was prepared.

First, the materials shown in Table 13 were mixed at the ratios shown in Table 13. Subsequently, 80 g of the ingredients for each hamburger was shaped in a flat circle, and then masses were measured. Subsequently, each hamburger was heated at 220° C. for 10 minutes, and then a mass was measured. Some were used for sensory evaluation, and some were used for a freezing test. Subsequently, each of the frozen hamburgers was heated at 220° C. for 20 minutes to thaw, a mass was measured, and sensory evaluation was performed.

TABLE 13

| | Blending ratio (parts by mass) | | | | |
|---|---|---|---|---|---|
| Food ingredient | Negative control | Preparation Example 8, 1 mass %-added group | Preparation Example 8, 2 mass %-added group | KC Flock, 1 mass %-added group | KC Flock, 2 mass %-added group |
| Minced beef and pork | 51.02 | 50.02 | 49.02 | 50.02 | 49.02 |
| Onion | 15.31 | 15.31 | 15.31 | 15.31 | 15.31 |
| Egg white | 6.33 | 6.33 | 6.33 | 6.33 | 6.33 |
| Bread crumbs | 5.10 | 5.10 | 5.10 | 5.10 | 5.10 |
| Vegetable soy protein | 2.04 | 2.04 | 2.04 | 2.04 | 2.04 |
| Starch | 1.02 | 1.02 | 1.02 | 1.02 | 1.02 |
| Soy sauce | 1.02 | 1.02 | 1.02 | 1.02 | 1.02 |
| Red wine | 1.02 | 1.02 | 1.02 | 1.02 | 1.02 |
| Sugar | 0.71 | 0.71 | 0.71 | 0.71 | 0.71 |
| Tomato ketchup | 0.51 | 0.51 | 0.51 | 0.51 | 0.51 |
| Table salt | 0.51 | 0.51 | 0.51 | 0.51 | 0.51 |
| Sodium glutamate | 0.10 | 0.10 | 0.10 | 0.10 | 0.10 |
| Water | 15.31 | 15.31 | 15.31 | 15.31 | 15.31 |
| Sample of Preparation Example 8 | — | 1.00 | 2.00 | — | — |
| KC Flock | — | — | — | 1.00 | 2.00 |
| Total | 100.0 | 100.0 | 100.0 | 100.0 | 100.0 |

Figure 2:
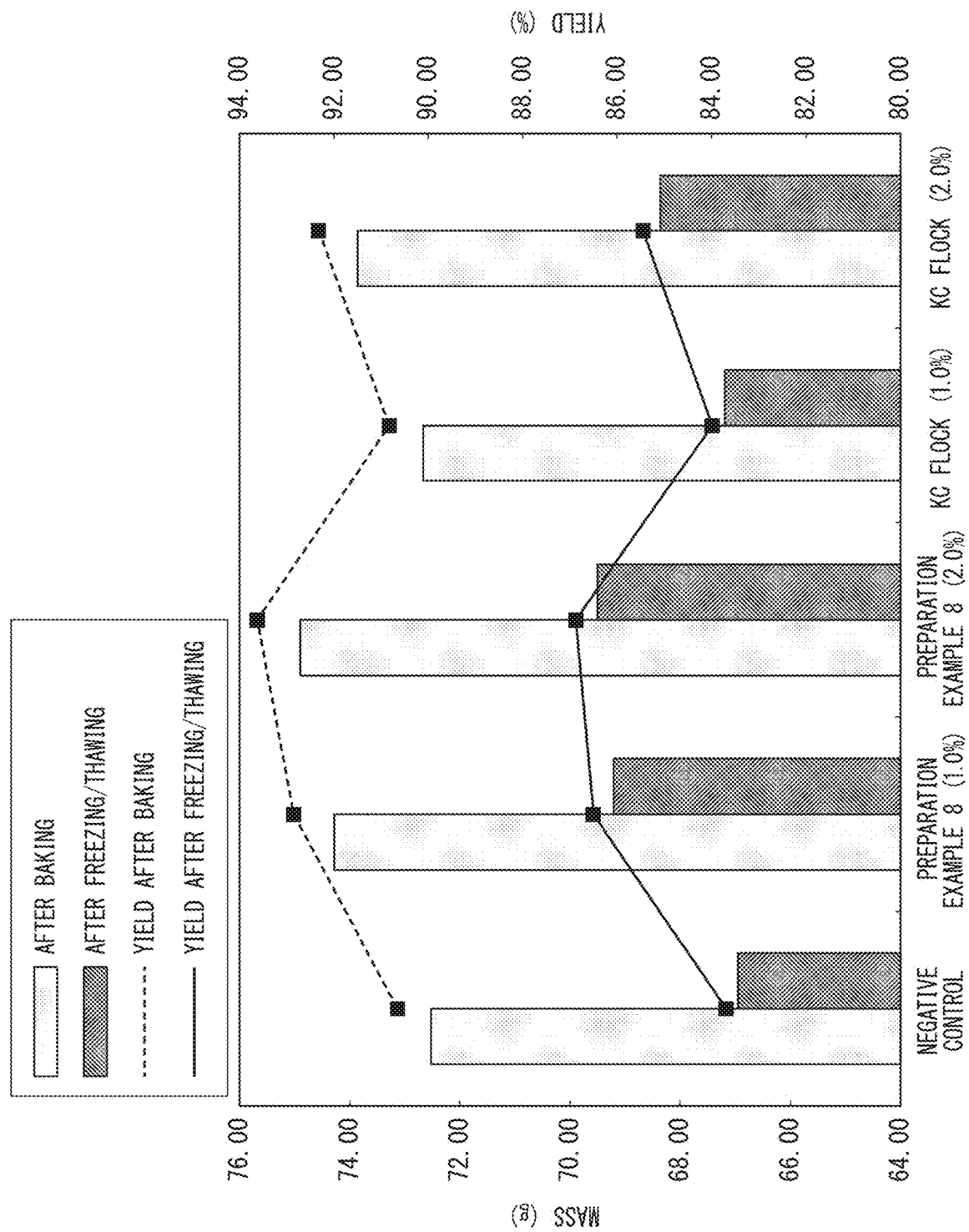
FIG. 2 is a graph representing the mass and yield of each hamburger.

FIG. 2 is a graph representing the mass and yield of each hamburger. The yield was enhanced approximately 3% by adding 1% by mass of the sample of Preparation Example 8 to the hamburger. In addition, when 2% by mass of the sample of Preparation Example 8 was added to the hamburger, texture was enhanced. Meanwhile, the KC Flock-added group exhibited a dry and tough texture. In addition, when the sample of Preparation Example 8 was added to the hamburgers, the yields were enhanced compared to the negative control, and there was no problem in freezing tolerance.

Experimental Example 18

(Evaluation as Quality Improving Material for Food 2)

The sample of Preparation Example 8 was added to tuna mayonnaise as a sample to evaluate the effect of preventing syneresis/oil separation. As a control, cellulose powder (trade name "KC Flock," produced by Nippon Paper Chemicals Co., Ltd.) was used. In addition, as a negative control, tuna mayonnaise in which neither the sample of Preparation Example 8 nor the cellulose powder was added was used.

First, tuna, oil, mayonnaise and water were mixed at ratios shown in Table 14 to manufacture tuna mayonnaise. Subsequently, each sample was blended at a ratio shown in Table 14 in the tuna mayonnaise. Such tuna mayonnaise was wrapped with a non-woven fabric, and hung above a funnel set in a graduated cylinder to collect a dropped liquid in the graduated cylinder.

Subsequently, based on the graduations of the graduated cylinder, an amount of syneresis/oil separation was measured over time, and then a syneresis/oil separation rate was calculated by the following formula.

Syneresis/oil separation rate (%)=Amount of syneresis/oil separation (g)/Total amount of tuna mayonnaise (g)×100

In addition, a syneresis/oil retention rate was calculated by the following formula.

Syneresis/oil retention rate (%)=100(%)−syneresis/oil separation rate (%)

TABLE 14

| | Blending ratio (parts by mass) | | | | |
| --- | --- | --- | --- | --- | --- |
| Food Ingredient | Negative control | Preparation Example 8, 1 mass %- added group | Preparation Example 8, 2 mass %- added group | KC Flock, 1 mass %- added group | KC Flock, 2 mass %- added group |
| Tuna | 51.13 | 51.13 | 51.13 | 51.13 | 51.13 |
| Oil | 14.30 | 14.30 | 14.30 | 14.30 | 14.30 |
| Mayonnaise | 29.80 | 29.80 | 29.80 | 29.80 | 29.80 |
| Water | 4.77 | 4.77 | 4.77 | 4.77 | 4.77 |
| Sample of Preparation Example 8 | — | 1.0 | 2.0 | — | — |
| KC Flock | — | — | — | 1.0 | 2.0 |
| Total | 100.0 | 101.0 | 102.0 | 101.0 | 102.0 |

Figure 3:
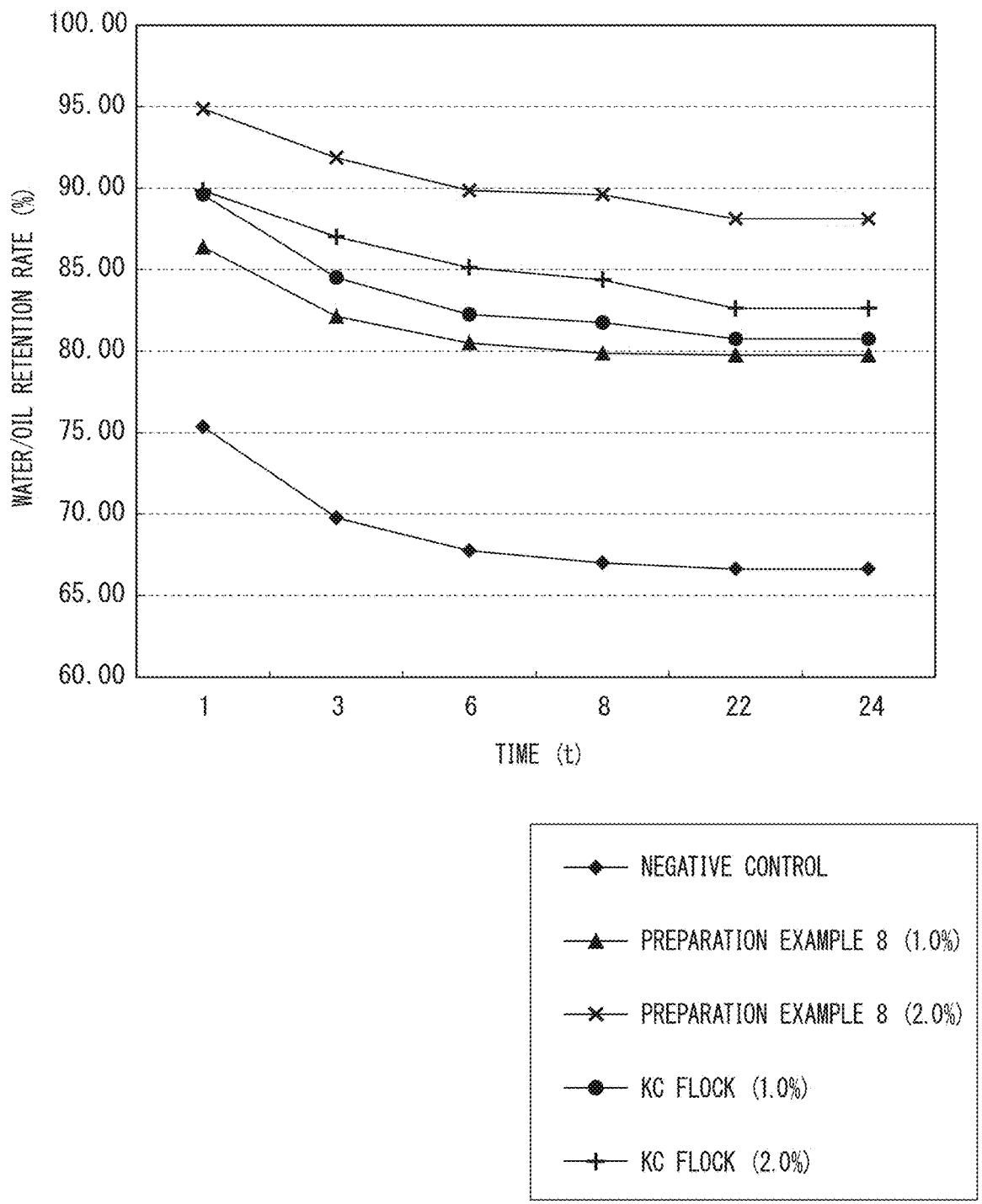
FIG. 3 is a graph representing the time-dependent change in a water retention/oil retention rate of each tuna mayonnaise.

FIG. 3 is a graph showing the time-dependent change in a water/oil retention rate of each tuna mayonnaise. The unit of the horizontal axis of the graph is hours. It was confirmed that the addition of the sample of Preparation Example 8 to the tuna mayonnaise exhibits a syneresis/oil separation inhibitory effect. Also, it was confirmed that the sample of Preparation Example 8 tends to exhibit higher water and oil retaining abilities than KC Flock, in the coexistence of water and oil. The inventors assume that such a tendency is caused by the shape of cells being maintained in the sample of Preparation Example 8 and thus water and oil is retained because of the function of a cell surface. Also, the inventors assume that the reason that the sample of Preparation Example 8 exhibits almost the same water retention and oil retention effects is because the shape of cells is maintained in the sample of Preparation Example 8.

Experimental Example 19

Preparation Example 9

Yeast cells were prepared without enzyme treatment or without using an emulsifier. As the yeast cells, a yeast extract residue generated by extracting a yeast extract from baker's yeast through hydrothermal extraction was used. First, the yeast cells were sterilized at 90 to 92° C. for 30 minutes. Subsequently, after cooling, the yeast cells were washed with water three times and then dried using a drum dryer. Subsequently, the yeast cells were crushed into powder with 50 mesh pass, thereby obtaining a sample of Preparation Example 9.

Experimental Example 20

(Evaluation as Quality Improving Material for Food 3)

Karaage powder was prepared by adding the sample of Preparation Example 8, the sample of Preparation Example 9 and commercially-available yeast cells (trade name "KR yeast," produced by KOHJIN Life Sciences Co., Ltd.) for evaluation. The "KR yeast" is a residue obtained by extracting a yeast extract from yeast of the *Candida* genus (torula yeast) (see Japanese Unexamined Patent Application Publication No. 2014-230540). First, karaage powders were prepared with the compositions shown in Table 15.

TABLE 15

| | Blending ratio (parts by mass) | | | |
| --- | --- | --- | --- | --- |
| Food ingredients | Negative control | Preparation Example 9- added group | KR yeast- added group | Preparation Example 8- added group |
| Potato starch | 100 | 95 | 95 | 95 |
| Sample of Preparation Example 9 | — | 5 | — | — |

TABLE 15-continued

| Food ingredients | Blending ratio (parts by mass) | | | |
| --- | --- | --- | --- | --- |
| | Negative control | Preparation Example 9-added group | KR yeast-added group | Preparation Example 8-added group |
| KR yeast | — | — | 5 | — |
| Sample of Preparation Example 8 | — | — | — | 5 |
| Total | 100 | 100 | 100 | 100 |

Subsequently, karaage was cooked using each of the prepared karaage powders, and then subjected to sensory evaluation. Specifically, first, the skin of chicken breast was removed, cut into pieces of approximately 20 g, and marinated in a soy sauce-based seasoning for 30 minutes. After marinating, the chicken breast was put on a sieve for 3 minutes to remove the marinade. Subsequently, the marinated chicken breast was covered with each karaage powder, and then fried in salad oil at 175° C. for 5 minutes.

Subsequently, the resulting karaage was tasted by 8 panelists to perform sensory evaluation. Evaluation items were the crispness of a crust and the juiciness of lean meat. As the result of a negative control (yeast cell-free group) was set as the reference, which is 3 points, the evaluation was scored as follows: very good (5 points), good (4 points), fair—the same as that of the negative control (3 points), poor (2 points), and very poor (1 point). Averages of the scores of the 8 panelists were calculated. In addition, taste assessment as karaage was evaluated as "total evaluation," categorized as good (5 points), fair, which is the same as that of the negative control (3 points), and unfavorable (1 point), and the averages of the average scores of the 8 panelists were calculated. The results are shown in Table 16.

TABLE 16

| | Negative control | Preparation Example 9-added group | KR yeast-added group | Preparation Example 8-added group |
| --- | --- | --- | --- | --- |
| Crispness of crust | 3 | 3.6 | 3.4 | 4.7 |
| Juiciness of lean meat | 3 | 4.1 | 3.5 | 4.6 |
| Total evaluation | 3 | 3.9 | 3.5 | 4.7 |

As a result, the karaage prepared using the karaage powder of the negative control was less crisp, and overall soggy. In addition, the karaage prepared using the karaage powders of Preparation Example 9-added group and the KR yeast-added group was slightly enhanced in crispness and thus improved in texture, but still maintained an overall soggy impression. On the contrary, the karaage prepared using the karaage powder of the Preparation Example 8-added group was clearly enhanced in crispness of a crust.

From the above results, it was found that, when yeast cells prepared by a preparation method including enzyme treatment and emulsifier addition were added to karaage powder, the crispness of the crust of the karaage was enhanced. Also, in terms of the juiciness of lean meat, it was confirmed that meat juiciness was significantly enhanced by adding the yeast cells to the karaage powder. For the effect of improving the juiciness of meat, the type of yeast cells seemed to be more influential than a degree of washing the yeast. Specifically, while the karaage prepared using the karaage powder of the torula yeast-derived KR yeast-added group was less enhanced in juiciness of meat in the karaage than that of the negative control, the karaage prepared using the karaage powders of the baker's yeast-derived Preparation Example 8-added group and the Preparation Example 9-added group was considerably enhanced in the juiciness of the karaage, compared to the negative control.

Experimental Example 21

(Evaluation as Quality Improving Material for Food 4)

Karaage powder to which the sample of Preparation Example 8, the sample of Preparation Example 9 and commercially-available yeast cells (trade name "KR yeast," produced by KOHJIN Life Sciences Co., Ltd.) were added to commercially-available karaage powder (trade name "Nisshin karaage powder," produced by Nisshin Foods Inc.) was prepared and evaluated. First, karaage powders having compositions shown in Table 17 were prepared.

TABLE 17

| Food ingredient | Blending ratio (parts by mass) | | | |
| --- | --- | --- | --- | --- |
| | Negative control | Preparation Example 9-added group | KR yeast-added group | Preparation Example 8-added group |
| Commercially-available karaage powder | 100 | 95 | 95 | 95 |
| Sample of Preparation Example 9 | — | 5 | — | — |
| KR yeast | — | — | 5 | — |
| Sample of Preparation Example 8 | — | — | — | 5 |
| Total | 100 | 100 | 100 | 100 |

Subsequently, as described in Experimental Example 20, the skin of chicken breast was removed, cut into pieces of approximately 20 g, and marinated with egg mixed with water. After marinating, the chicken breast was coated with each karaage powder, and fried in salad oil at 175° C. for 4.5 minutes. The resulting karaage was tasted by 8 panelists to perform sensory evaluation. Evaluation items and criteria were the same as those described in Experimental Example 20. Results are shown in Table 18.

TABLE 18

| | Negative control | Preparation Example 9-added group | KR yeast-added group | Preparation Example 8-added group |
| --- | --- | --- | --- | --- |
| Crispness of crust | 3 | 3.9 | 3.5 | 4.8 |
| Juiciness of lean meat | 3 | 4.3 | 3.7 | 4.9 |
| Total evaluation | 3 | 4.1 | 3.6 | 4.9 |

From these results, even when the commercially-available karaage powder was used, the same results as shown in Experimental Example 20 were obtained. Specifically, karaage prepared using the karaage powder of Preparation Example 8-added group was enhanced in the crispness of a crust, compared to karaage using other karaage powders. Also, karaage using karaage powders of the Preparation Example 8-added group derived from baker's yeast and the Preparation Example 9-added group was considerably enhanced in juiciness, compared to that of the negative control.

From the above results, it was shown that, even when the sample of Preparation Example 8 was added to the commercially-available tempura powder, the crispness of a crust and the juiciness of lean meat of karaage were clearly enhanced. In addition, it was considered that, in Experimental Example 20, the water value of a food material was increased by marinating chicken breast in a seasoning, but the yeast cells added to the karaage powder were not able to hold water in the food material, and the crust became soggy.

Experimental Example 22

(Evaluation as Quality Improving Material for Food 5)

Using the sample of Preparation Example 8, karaage was cooked by a different cooking method from those described in Experimental Example 20 and Experimental Example 21, and then sensory evaluation was performed. First, dusting powder with the composition shown in Table 19, batter with the composition shown in Table 20 and breading with the composition shown in Table 21 were prepared.

TABLE 19

Dusting powder

| | Blending ratio (parts by mass) | |
|---|---|---|
| Food ingredient | Negative control | Preparation Example 8-added group |
| Starch | 76 | 71 |
| Wheat flour | 21.2 | 21.2 |
| Table salt | 1.5 | 1.5 |
| Seasoning (amino acid) | 1 | 1 |
| Spices | 0.3 | 0.3 |
| Sample of Preparation Example 8 | — | 5 |
| Total | 100 | 100 |

TABLE 20

Batter

| Food ingredient | Blending ratio (parts by mass) |
|---|---|
| Wheat flour | 26.4 |
| Soy sauce | 5 |
| Mirin (sweet sake) | 1 |
| Vegetable oil | 3 |
| Table salt | 0.4 |
| Seasoning (amino acid) | 0.4 |
| Spices | 0.4 |
| Water | 63.4 |
| Total | 100 |

TABLE 21

Breading

| | Blending ratio (parts by mass) | |
|---|---|---|
| Food ingredient | Negative control | Preparation Example 8-added group |
| Starch | 71.5 | 66.5 |
| Wheat flour | 25.5 | 25.5 |
| Table salt | 1 | 1 |

TABLE 21-continued

Breading

| | Blending ratio (parts by mass) | |
|---|---|---|
| Food ingredient | Negative control | Preparation Example 8-added group |
| Seasoning (amino acids) | 2 | 2 |
| Sample of Preparation Example 8 | 0 | 5 |
| Total | 100 | 100 |

Subsequently, the skin of chicken breast was removed, and cut into pieces of approximately 20 g. Subsequently, the cut chicken meat was marinated with a soy sauce-based seasoning. Subsequently, the chicken breast marinated with the seasoning was sequentially covered with the dusting powder, the batter and the breading mentioned above to make a crust, and then was quickly frozen. More specifically, a group sequentially coated with negative control dusting powder, batter and the negative control breading (negative control), a group sequentially coated with the dusting powder of the Preparation Example 8-added group, the batter and the negative control breading (dusting powder-added group), and a group sequentially coated with the negative control dusting powder, the batter and the breading of the Preparation Example 8-added group (breading-added group) were prepared.

Subsequently, each of the coated chicken breasts was stored in a freezer for approximately 1 week, and then fried in salad oil at 175° C. for 6 minutes. The resulting karaage was tasted by 8 panelists to perform sensory evaluation. Evaluation items and criteria were the same as described in Experimental Example 20. Results are shown in Table 22.

TABLE 22

| | Negative control | Dusting powder-added group | Breading-added group |
|---|---|---|---|
| Crispness of crust | 3 | 4 | 4.5 |
| Juiciness of lean meat | 3 | 4.4 | 3.5 |
| Total evaluation | 3 | 4.2 | 4.0 |

As a result, compared to the negative control, in the dusting powder-added group or the breading-added group, the crispness of a crust and the juiciness of lean meat of karaage were clearly enhanced. The karaage of the dusting powder-added group in which the sample of Preparation Example 8 was added to the dusting powder directly covered on the chicken meat was considerably enhanced in the juiciness of lean meat. It seems that this is because the sample of Preparation Example 8 holds water from the chicken meat.

Meanwhile, the karaage of the breading-added group in which the sample of Preparation Example 8 was added to the breading was considerably enhanced in the crispness of a crust, compared to the juiciness of lean meat. It seems that this is because the breading is the outermost coating.

Experimental Example 23

(Evaluation as Quality Improving Material for Food 6)

Tempura was cooked using the sample of Preparation Example 8 to perform sensory evaluation. First, tempura powder with the composition shown in Table 23 was prepared. In addition, tempura powder prepared by adding 1% by mass of the sample of Preparation Example 8 to the tempura powder with the composition shown in Table 23 (group to which 1% by mass of the Preparation Example 8 was added), and tempura powder prepared by adding 2% by mass of the sample of Preparation Example 8 to the tempura powder with the composition shown in Table 23 (group to which 2% by mass of the Preparation Example 8 was added) were prepared.

TABLE 23

| | Blending ratio (parts by mass) | | |
| --- | --- | --- | --- |
| Food ingredient | Wheat flour, processed starch group | Wheat flour, baking powder group | Wheat Flour, processed starch, baking powder group |
| Wheat flour | 90 | 99 | 89 |
| Processed starch (phosphorylated cross-linking) | 10 | — | 10 |
| Baking powder | — | 1 | 1 |

Subsequently, sweet potato sticks with a size of 1 cm×1 cm×4 cm were coated with a coating prepared by mixing a suitable amount of cold water with the above-described tempura powder, and fried in salad oil at 180° C. for 2.5 minutes. Subsequently, the resulting tempura was tasted by 8 panelists to perform sensory evaluation. An evaluation item was the crispness of a crust, and evaluation criteria were the same as those used in Experimental Example 20. Results are shown in Table 24. The sensory evaluation was carried out immediately after cooking or 1 hour after cooking in which the tempura was allowed to stand at room temperature.

TABLE 24

| | Non-added group | | Preparation Example 8, 1 mass %-added group | | Preparation Example 8, 2 mass %-added group | |
| --- | --- | --- | --- | --- | --- | --- |
| | After cooking | 1 hr later | After cooking | 1 hr later | After cooking | 1 hr later |
| Wheat flour, processed starch group | 3 | 2.0 | 4.2 | 2.5 | 4.5 | 2.5 |
| Wheat flour, baking powder group | 3 | 2.5 | 4.2 | 4.0 | 4.5 | 3.0 |
| Wheat flour, processed starch, baking powder group | 3 | 2.5 | 4.5 | 4.0 | 4.8 | 3.0 |

As a result, the tempura of the Preparation Example 8-added group prepared immediately after cooking was enhanced in the crispness of a crust, compared to the tempura of the non-added group, regardless of an amount of the sample of Preparation Example 8 added to the tempura powder. In addition, the tempura of the Preparation Example 8-added group, which had been allowed to stand for 1 hour after cooking, was enhanced in the crispness of a crust especially using the baking powder-added tempura powder, compared to that of the non-added group.

Experimental Example 24

(Evaluation as Quality Improving Material for Food 7)
Croquettes were cooked using the sample of Preparation Example 8 to perform sensory evaluation. First, batter with the composition shown in Table 25 was prepared.

TABLE 25

| | Batter | | |
| --- | --- | --- | --- |
| | Blending ratio (parts by mass) | | |
| Food ingredient | Negative control | Preparation Example 8, 0.25 mass %-added group | Preparation Example 8, 0.5 mass %-added group |
| Batter mix (see below) | 100 | 100 | 100 |
| Sample of Preparation Example 8 | — | 1 | 2 |
| Salad oil | 20 | 20 | 20 |
| Water | 280 | 280 | 280 |
| Total | 400 | 401 | 402 |

| Batter mix | |
| --- | --- |
| Food ingredient | Blending ratio (parts by mass) |
| Starch | 61.4 |
| Wheat flour | 20.0 |
| Dextrin | 5.0 |
| Shortening | 4.0 |
| Soybean powder | 4.0 |
| Vegetable oil | 3.0 |
| Vegetable protein | 1.3 |
| Thickening polysaccharides | 0.7 |
| Processed starch | 0.5 |
| Emulsifier | 0.1 |
| Total | 100.0 |

Subsequently, raw ingredients for croquettes were prepared using 80 parts by mass of potato, 15 parts by mass of minced beef, 15 parts by mass of onion, table salt, a small amount of pepper as ingredients, and shaped according to a conventional method. Subsequently, the shaped croquette raw ingredients were coated with primary bread crumbs, coated with the batter described above and then with secondary bread crumbs, and quickly frozen, thereby preparing frozen croquettes.

The croquettes stored in a frozen state for several weeks were fried in salad oil at 170° C. for 4 minutes. The resulting croquettes were allowed to stand at room temperature for 3 hours, and tasted by 8 expert panelists to perform sensory evaluation. An evaluation item was the crispness of a crust, and evaluation criteria were the same as those used in Experimental Example 20. As a result, compared to the croquettes using the negative control batter, the Preparation Example 8-added group croquettes were enhanced in crispness of a crust.

Experimental Example 25

(Evaluation as Quality Improving Material for Food 8)
Pork loin ham was prepared using the sample of Preparation Example 8 to perform sensory evaluation. First, a pickling liquid with the composition shown in Table 26 was prepared.

TABLE 26

| Food ingredient | Blending ratio (parts by mass) | |
| --- | --- | --- |
| | Negative control | Preparation Example 8- added group |
| Table salt | 17.1 | 17.1 |
| Sample of Preparation Example 8 | — | 10.0 |
| Sugar | 1.7 | 1.7 |
| Nitrates | 0.7 | 0.7 |
| Phosphates | 0.9 | 0.9 |
| Sodium erythorbate | 0.9 | 0.9 |
| Sodium glutamate | 1.2 | 1.2 |
| Water | 77.5 | 67.5 |
| Total | 100 | 100 |

Subsequently, the pork loin ham was cut to an appropriate size and each of the above-described pickling liquids was injected using a syringe at an injection ratio of 120% with respect to the mass of raw meat. In addition, the injection ratio was calculated by the following formula.

Injection ratio (%)=Mass of raw meat after injection/ Mass of raw meat before injection×100

Subsequently, following the injection, the raw meat was aged for 1 hour, and then filled in a casing. Subsequently, the raw meat filled in the casing was cut to a thickness of 1 cm and then vacuum-packed, followed by thermal treatment by boiling at 80° C. for 5 hours, resulting in cooked pork loin ham.

Subsequently, the resulting cooked pork loin ham was tasted by 10 panelists to perform sensory evaluation. Evaluation items were the softness of lean meat and the juiciness of lean meat. The softness of lean meat was evaluated as 5 points when the meat is very softer to easily chew, 4 points when the meat is softer, 3 points when the meat is fair (the same as the negative control), 2 points when the meat is tough, or 1 point when the meat is too tough to easily chew.

In addition, as the result of the negative control (yeast cells of the non-added group) was set as the reference, which is 3 points, the juiciness of meat was evaluated as 5 points (very good), 4 points (good), 3 points (fair, the same as the negative control), 2 points (poor), and 1 point (very poor), and an average of the scores of the 10 panelists was calculated.

In addition, taste assessment as the pork loin ham was evaluated as "total evaluation," which was categorized as 5 points (good), 3 points (fair, which is the same as that of the negative control), and 1 point (unfavorable), and an average of the average scores of the 10 panelists was calculated. Results are shown in Table 27.

TABLE 27

| | Negative control | Preparation Example 8- added group |
| --- | --- | --- |
| Softness of lean meat | 3 | 4.9 |
| Juiciness of lean meat | 3 | 5.0 |
| Total evaluation | 3 | 5.0 |

As a result, the pork loin ham prepared using the pickling liquid of Preparation Example 8-added group was considerably enhanced in softness of lean meat and juiciness of meat, compared to the negative control pickling liquid.

Regarding the softness of lean meat, the meat was easy to chew at first and maintained softness during chewing, and thus the entire pork loin ham produced above had a soft texture in the mouth.

From the above results, it was found that the addition of yeast cells to the lean meat product such as pork loin ham enhances the juiciness due to the above-described water/oil retention effects, and actually softens tissue of the lean meat.

Experimental Example 26

(Evaluation as Quality Improving Material for Food 9)

Pork loin cutlets were prepared using the sample of Preparation Example 8 to perform sensory evaluation. First, pickling liquids with the compositions shown in Table 28 were prepared. For a pickling liquid as a negative control, a protein preparation (trade name "New Fuji Pro 3000," produced by Fuji Oil Co., Ltd.) was added, instead of the sample of Preparation Example 8.

TABLE 28

| Food ingredient | Blending ratio (parts by mass) | |
| --- | --- | --- |
| | Negative control | Preparation Example 8- added group |
| Phosphates | 1.0 | 1.0 |
| Protein preparation | 10 | 1.5 |
| Sample of Preparation Example 8 | — | 8.50 |
| Dextrin | 4.00 | 4.00 |
| Wheat starch | 4.00 | 4.00 |
| Sodium glutamate | 0.30 | 0.30 |
| Enzymatic preparation | 0.40 | 0.40 |
| Salinity | 1.50 | 1.50 |
| Water | 78.80 | 78.80 |
| Total | 100.00 | 100.00 |

Subsequently, the pork loin for pork cutlets was cut into pieces of approximately 130 g, each pickling liquid described above was injected using a syringe at an injection ratio of 125% to 131% with respect to the mass of raw meat. In addition, a method of calculating the injection ratio is the same as described above.

Subsequently, the lean meat to which the pickling liquid was injected was tumbled and thereafter coated with dusting powder, batter and bread crumbs, and then fried in salad oil at 175° C. for 7 minutes. The resulting pork cutlet was tasted by 10 panelists to perform sensory evaluation. Evaluation items were the softness, the juiciness and the taste of lean meat. As the results of the negative control were set as the reference, which is 3 points, the evaluation was scored as 5 points (very good), 4 points (good), 3 points (fair, the same as the negative control), 2 points (poor), and 1 point (very poor), and an average of the scores of the 10 panelists was calculated. In addition, the average of the average score for each of the softness of lean meat, the juiciness of lean meat and the taste results was calculated as "total evaluation." The results are shown in Table 29.

TABLE 29

|  | Negative control | Preparation Example 8-added group |
|---|---|---|
| Softness of lean meat | 3 | 4.9 |
| Juiciness of lean meat | 3 | 5.0 |
| Taste | 3 | 3.2 |
| Total evaluation | 3 | 4.4 |

As a result, the pork cutlet prepared using the pickling liquid of the Preparation Example 8-added group was considerably enhanced in softness and juiciness of lean meat, compared to that of the negative control pickling liquid. Meanwhile, it was not confirmed that there was a great difference in taste of lean meat between the pork cutlet prepared using the negative control pickling liquid, and the pork cutlet prepared using the pickling liquid of the Preparation Example 8-added group.

In addition, the pork cutlets were allowed to stand for 30 minutes after cooking, and then examined again with respect to the softness of lean meat. Consequently, in the case of the pork cutlet prepared using the negative control pickling liquid, the meat was becoming tougher over time, but in the case of the pork cutlet prepared using the pickling liquid of the Preparation Example 8-added group, the meat was soft as if it had been just fried, even a few hours after the cooking.

From the above results, it was found that the injection of the pickling liquid to which the sample of Preparation Example 8 was added does not exhibit an influence on the taste of lean meat itself, but on the softness and juiciness of lean meat.

In addition, a breaking strength was measured with respect to each of the pork cutlets prepared using the pickling liquid to which the sample of Preparation Example 8 and the negative control pickling liquid according to the same method as described above using a texture analyzer (trade name "TA.XT. plus texture analyzer," produced by Stable Micro Systems). As a plunger, a wedge type plunger (Model No. 49, produced by Yamaden Co., Ltd.) was used.

Figure 4:
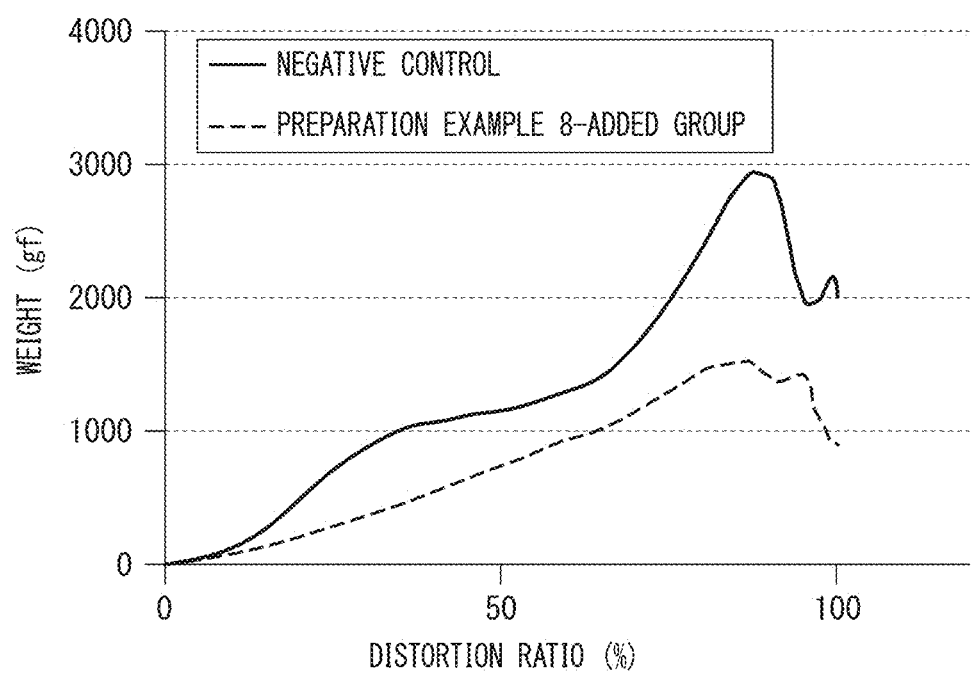
FIG. 4 is a graph representing a breaking strength curve in Experimental Example 26.

FIG. 4 is a graph showing the breaking strength curves measured above. As a result, it was found that the pork cutlet prepared using the negative control pickling liquid exhibits a breaking strength of approximately 3000 gf at the highest peak of the breaking strength curve. Meanwhile, it was found that the pork cutlet prepared using the pickling liquid of the Preparation Example 8-added group exhibits a breaking strength of approximately 1500 gf at the highest peak of the breaking strength curve, which is approximately a half of that of the negative control.

Even from the above results, it is clear that the texture of the pork cutlet prepared using the pickling liquid of the Preparation Example 8-added group is considerably more soft than that using the negative control pickling liquid.

Figure 5A:
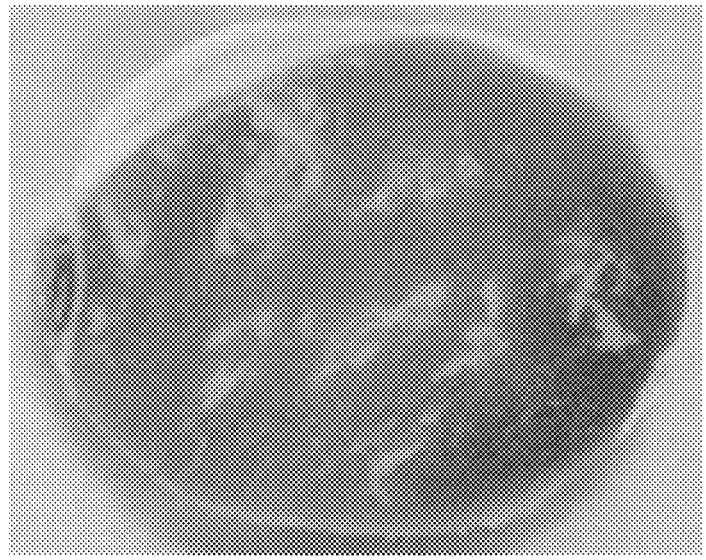
FIG. 5A is a photograph showing a section of pork loin after injecting a negative control pickling liquid according to Experimental Example 26.
Figure 5B:
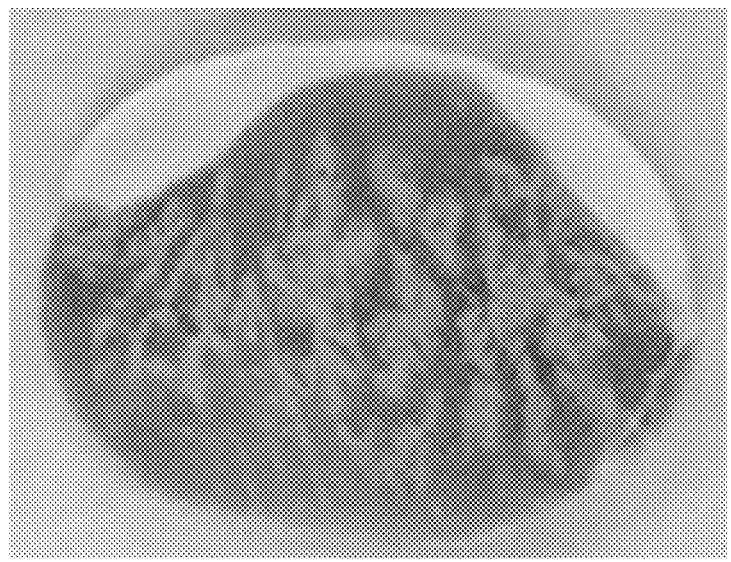
FIG. 5B is a photograph showing a section of pork loin after injecting a pickling liquid of an addition group in Preparation Example 8, according to Experimental Example 26.

Subsequently, the cross-section of the pork loin obtained after each of the pickling liquids of the Preparation Example 8-added group and the negative control was injected was observed. FIG. 5A is a cross-sectional view of the pork loin obtained after the negative control pickling liquid was injected, and FIG. 5B is a cross-sectional view of the pork loin obtained after pickling liquid of the Preparation Example 8-added group was injected.

As a result, surprisingly, compared to the pork loin obtained after injection of the negative control pickling liquid, in the pork loin obtained after the pickling liquid of the Preparation Example 8-added group was injected, the pickling liquid was evenly dispersed throughout the lean meat. From the above result, it can be seen that, the use of the sample of Preparation Example 8 allows the pickling liquid to be dispersed throughout the lean meat, and makes the entire lean meat soft.

Experimental Example 27

(Evaluation as Quality Improving Material for Food 10)

The effect of marinating fish meat with a marinade containing the sample of Preparation Example 8 was examined. The effect of marinating fish meat with marinades respectively containing the sample of Preparation Example 9, a cellulose preparation (trade name "KC Flock," produced by Nippon Paper Chemicals Co., Ltd.), a protein preparation (trade name "New Fuji Pro 3000," produced by Fuji Oil Co., Ltd.), and KR yeast (trade name, produced by KOHJIN Life Sciences Co., Ltd.) was also examined.

First, a marinade was prepared by adding 2 parts by mass of table salt, and 2 parts by mass of the sample of Preparation Example 8, the sample of Preparation Example 9, the cellulose preparation, the protein preparation, or the KR yeast to 100 parts by mass of water. As a negative control, a marinade prepared by adding 2 parts by mass of table salt to 100 parts by mass of water was used.

Subsequently, a marlin fillet was marinated with each marinade for 3 hours. Subsequently, the marlin fillet was taken out of the marinade, sequentially coated with wheat flour, egg and bread crumbs, and then fried in salad oil at 175° C. for 3 minutes.

The resulting fried marlin was tasted by 8 panelists to perform sensory evaluation. Evaluation items were the softness of lean meat and the juiciness of lean meat. As the result of the negative control was rated as C, the evaluation was categorized as very good (A), good (B), fair, the same as the negative control (C), and poor (D), and results obtained by 8 panelists were summarized. The results are shown in Table 30.

TABLE 30

|  | Negative control | Preparation Example 9-added group | Cellulose preparation-added group | Protein preparation-added group | KR yeast-added group | Preparation Example 8-added group |
|---|---|---|---|---|---|---|
| Softness of lean meat | C | C | C | C | C | A |
| Juiciness of lean meat | C | B | D | C | C | A |

As a result, compared to the fried marlin marinated with that of the negative control, the fried marlin marinated with the marinade of the Preparation Example 8-added group was considerably enhanced in softness of lean meat. Meanwhile, a difference between the fried marlin marinated with other marinades, excluding that of the Preparation Example 8-added group, and the fried marlin marinated with the marinade of the negative control was not found.

In addition, the fried marlins marinated with the marinades of the Preparation Example 8-added group and the Preparation Example 9-added group were enhanced in juiciness of lean meat, compared to the fried marlin marinated with the marinade of the negative control, and such an effect was clearly exhibited particularly in the fried marlin marinated with the marinade of the Preparation Example 8-added group.

Meanwhile, compared to the fried marlin marinated with the marinade of the negative control, in the fried marlin marinated with other marinades, excluding those of the Preparation Example 8-added group and the Preparation Example 9-added group, enhancement in juiciness of lean meat was not detected, and particularly, it was undesirable to marinate the fried marlin with the marinade of the cellulose preparation-added group because of the resulting brittleness.

From the above results, it was found that, particularly, the baker's yeast-derived yeast cells have an effect of enhancing the juiciness of meat. Meanwhile, simple yeast cells exhibited a low effect of softening lean meat, and to exhibit a high effect of softening lean meat, it was thought that the yeast cells need to be treated with an enzyme, an emulsifier or the like.

Experimental Example 28

(Evaluation as Quality Improving Material for Food 11)

Effects exhibited when chicken meat was marinated with the marinade containing the sample of Preparation Example 8 were examined. The effect of marinating chicken meat with marinade respectively containing the sample of Preparation Example 9, a cellulose preparation (trade name "KC Flock," produced by Nippon Paper Chemicals Co., Ltd.), a protein preparation (trade name "New Fuji Pro 3000," produced by Fuji Oil Co., Ltd.), and KR yeast (trade name, produced by KOHJIN Life Sciences Co., Ltd.) was also examined.

First, a soy sauce-based seasoning liquid containing 2% by mass of the sample of Preparation Example 8, the sample of Preparation Example 9, a cellulose preparation, a protein preparation or KR yeast was prepared. As a negative control, a soy sauce-based seasoning liquid, which does not contain any of these quality improving material for foods, was used.

Subsequently, the skin of chicken breast was removed, cut into pieces of approximately 20 g, and then marinated with each of the seasoning liquids for 30 minutes. Subsequently, the marinated chicken breast was put on a sieve for 3 minutes to remove the seasoning liquid. Subsequently, the marinated chicken breast was coated with potato starch, and then fried in salad oil at 175° C. for 4 minutes.

The resulting karaage was tasted by 8 panelists to perform sensory evaluation. Evaluation items were the softness of lean meat and the juiciness of lean meat. As the result obtained by the negative control was rated as C, and the evaluation was categorized as very good (A), good (B), fair, the same as the negative control (C), and poor (D), and results obtained by 8 panelists were summarized. The results are shown in Table 31.

TABLE 31

| | Negative control | Preparation Example 9-added group | Cellulose preparation-added group | Protein preparation-added group | KR yeast-added group | Preparation Example 8-added group |
|---|---|---|---|---|---|---|
| Softness of lean meat | C | B | C | C | C | A |
| Juiciness of lean meat | C | B | D | C | B | A |

As a result, the karaage marinated with the seasoning liquid of the Preparation Example 8-added group was considerably enhanced in softness of lean meat, compared to the karaage marinated with the seasoning liquid of the negative control. In addition, it was confirmed that, in the karaage marinated with the seasoning liquid of the Preparation Example 9-added group to which the sample of Preparation Example 9, derived from the baker's yeast which is the same as used in Preparation Example 8, was added without treatment with an enzyme or emulsifier, a slight effect of softening lean meat was exhibited. Meanwhile, karaage marinated with a seasoning liquid, rather than that of the Preparation Example 8-added group or the Preparation Example 9-added group, did not have a difference from the karaage marinated with the seasoning liquid of the negative control.

In addition, the karaage marinated with the seasoning liquid of the Preparation Example 8-added group was considerably enhanced in juiciness of lean meat, compared to that marinated with the seasoning liquid of the negative control.

In addition, in the karaage marinated with each of the seasoning liquids of the Preparation Example 9-added group and the KR yeast-added group, to which yeast cells were added, some enhancement in juiciness of lean meat was confirmed, but in the karaage marinated with a seasoning liquid, rather than those mentioned above, the enhancement in juiciness of meat was not confirmed.

From the above results, it can be seen that the yeast cells exhibit a certain effect on the juiciness of meat induced by the water and oil retention effects.

In addition, compared to different commercially-available quality improving material for foods, it was identified that simple yeast cells have a certain effect of enhancing the juiciness of meat, but do not have an effect of softening lean meat, which is a noticeable effect only confirmed from the sample of Preparation Example 8.

Experimental Example 29

(Evaluation as Quality Improving Material for Food 12)

Effects exhibited when chicken meat was marinated with a marinade to which the sample of Preparation Example 8 was added were examined. First, a mixed liquid was prepared with the composition shown in Table 32. As Control 1, a mixed liquid without yeast cells was prepared. In addition, Control 2, a mixed liquid containing sodium bicarbonate known to soften lean meat, but not yeast cells, was prepared.

TABLE 32

| Food ingredient | Blending ratio (parts by mass) | | |
| --- | --- | --- | --- |
| | Control 1 | Control 2 | Preparation Example 8-added group |
| Sodium bicarbonate | — | 20.0 | 20.0 |
| Soft brown sugar | 40.0 | 40.0 | 40.0 |
| Table salt | 15.0 | 15.0 | 15.0 |
| Lemon powder | 5.0 | 5.0 | 5.0 |
| White pepper | 3.0 | 3.0 | 3.0 |
| Chicken extract | 4.0 | 4.0 | 4.0 |
| Yeast extract | 1.0 | 1.0 | 1.0 |
| Soy sauce powder | 0.5 | 0.5 | 0.5 |
| Sample of Preparation Example 8 | — | — | 10.0 |
| Dextrin | 31.5 | 11.5 | 1.5 |
| Total | 100.0 | 100.0 | 100.0 |

Subsequently, the skin of chicken breast was removed, and marinated for 3 hours with a marinade prepared by diluting the mixed liquid 10 times with water. Subsequently, the marinated chicken breast was steamed at 100° C. for 20 minutes, thereby obtaining salad chicken. After heating, each salad chicken was cooled and vacuum-packed, and then stored in a refrigerator.

Subsequently, the resulting salad chicken was tasted by 8 panelists to perform sensory evaluation. Evaluation items were the softness of lean meat, the juiciness of lean meat and meat texture. As the result of Control 1 was scored as 3 points, the evaluation was scored as very good (5 points), good (4 points), fair, the same as Control 1 (3 points), poor (2 points) and very poor (1 point), and an average of the scores of the 8 panelists was calculated. Also, averages of average scores for the softness of lean meat, the juiciness of lean meat and the meat texture were calculated as "total evaluation." The results are shown in Table 33.

TABLE 33

| | Control 1 | Control 2 | Preparation Example 8-added group |
| --- | --- | --- | --- |
| Softness of lean meat | 3 | 4.2 | 4.5 |
| Juiciness of lean meat | 3 | 3.7 | 4.4 |
| Meat texture | 3 | 2.3 | 4.6 |
| Total evaluation | 3 | 3.4 | 4.5 |

In the salad chicken marinated with the marinade of Control 2 to which sodium bicarbonate was added, which is known to soften lean meat, and the salad chicken marinated with the marinade of the Preparation Example 8-added group, enhancement in softness of lean meat and juiciness of meat was confirmed. Among the salad chickens, the salad chicken marinated with the marinade of the Preparation Example 8-added group had the texture of lean meat, was easily chewed, and was enhanced in juiciness of meat.

While the salad chicken marinated with the marinade of Control 2 was soft, it did not have a favorable texture (fibrous, etc.), which is a unique feature of lean meat, but not like the featureless texture of terrine, and therefore the texture was not preferable as salad chicken.

Also, in cooking of the salad chicken, a mass of the salad chicken was weighed before marinating and after heating and storage in a refrigerator to evaluate a mass change (yield). The yield was calculated by the following formula.

Yield (%)=100×Weight of food ingredient after heating/cooling (g)/Weight of food ingredient before marinating (g)

As a result, the yield of the salad chicken marinated with the marinade of Control 1 was 75.0%. In addition, the yield of the salad chicken marinated with the marinade of Control 2 was 81.5%. Moreover, the yield of the salad chicken marinated with a marinade of the Preparation Example 8-added group was 82.7%.

Both Control 2 and the Preparation Example 8-added group were enhanced in yield, compared to Control 1, and among them, the Preparation Example 8-added group obtained the highest yield. It was thought that the enhancement in yield was influenced by the water and oil-retaining effect of the yeast cells.

Experimental Example 30

(Evaluation as Quality Improving Material for Food 13)
Effects obtained when beef was marinated with a marinade to which the sample of Preparation Example 8 was added were examined. First, a mixed liquid was prepared with the composition shown in Table 34. As Control 1, a mixed liquid without yeast cells was prepared. Also, as Control 2, a mixed liquid which contains sodium bicarbonate known to soften lean meat, and does not contain yeast cells was prepared.

TABLE 34

| Food ingredient | Blending ratio (parts by mass) | | |
| --- | --- | --- | --- |
| | Control 1 | Control 2 | Preparation Example 8-added group |
| Sodium bicarbonate | — | 20.0 | 20.0 |
| Soft brown sugar | 40.0 | 40.0 | 40.0 |
| Yeast extract | 4.0 | 4.0 | 4.0 |
| Sample of Preparation Example 8 | — | — | 10.0 |
| Dextrin | 56.0 | 36.0 | 26.0 |
| Total | 100.0 | 100.0 | 100.0 |

Subsequently, beef was cut to approximately 2 $cm^3$, and marinated for 3 hours with a marinade prepared by diluting the mixed liquid 10 times with water. Subsequently, the beef was taken out of the marinade, and then heated and baked in an oven at 250° C. for 15 minutes.

Subsequently, the resulting baked beef was tasted by 8 panelists to perform sensory evaluation. Evaluation items were the softness of lean meat, the juiciness of lean meat and a meat texture. As the result of Control 1 was scored as 3 points, evaluation was categorized as very good (5 points), good (4 points), fair, the same as Control 1 (3 points), poor (2 points) and very poor (1 point), and the averages of scores of the 8 panelists were calculated. Also, averages of average scores for the softness of lean meat, the juiciness of lean meat and the meat texture were calculated as "total evaluation." The results are shown in Table 35.

TABLE 35

| | Control 1 | Control 2 | Preparation Example 8 - added group |
| --- | --- | --- | --- |
| Softness of lean meat | 3 | 4.0 | 4.7 |
| Juiciness of lean meat | 3 | 3.8 | 4.3 |
| Meat texture | 3 | 2.3 | 4.6 |
| Total evaluation | 3 | 3.4 | 4.5 |

When beef was used, it was confirmed that, in the baked beef marinated with the marinade of Control 2 and the baked beef marinated with a marinade of the Preparation Example 8-added group, the softness of lean meat and the juiciness of meat were enhanced. However, in the baked beef marinated with the marinade of Control 2, sodium bicarbonate had an influence on the taste of lean meat, and the meat was soft but had a chemical taste like a rubber, which was not preferable for a meat texture.

In contrast, the baked beef marinated with a marinade of the Preparation Example 8-added group did not affect the taste of lean meat, but was juicy and soft while maintaining the original texture of beef and proper fibrosity, which was preferable for beef.

In addition, in cooking of the baked beef, the yield was examined. The yield was calculated in the same manner as described in Experimental Example 29. As a result, the yield of the baked beef marinated with the marinade of Control 1 was 57.7%. In addition, the yield of the baked beef marinated with the marinade of Control 2 was 58.6%. In addition, the yield of the baked beef marinated with the marinade of the Preparation Example 8-added group was 63.9%.

While there was no significant difference in yield between Control 2 and Control 1, the yield of the Preparation Example 8-added group was considerably enhanced.

Experimental Example 31

(Evaluation as Quality Improving Material for Food 14)

Effects exhibited when squid was marinated with a marinade to which the sample of Preparation Example 8 was added were examined. First, marinades were prepared with the compositions shown in Table 36. In addition, as a negative control, a marinade containing sodium bicarbonate known to soften lean meat, but not yeast cells, was prepared.

TABLE 36

| | Blending ratio (parts by mass) | |
|---|---|---|
| Food ingredient | Negative control | Preparation Example 8-added group |
| Sodium bicarbonate | 20 | 20 |
| Soft brown sugar | 40 | 40 |
| Sample of Preparation Example 8 | — | 10 |
| Dextrin | 40 | 30 |
| Total | 100 | 100 |

Subsequently, frozen squid was semi-thawed at room temperature, and then cut into pieces with a size of approximately 30 cm (length)×approximately 10 cm (width). The squid pieces were marinated with each marinade described above overnight. Subsequently, the squid pieces taken out of the marinade were heated in a steam oven at 100° C. for 10 minutes.

Subsequently, the resulting heated squid was tasted by 8 panelists to perform sensory evaluation. Evaluation items were the softness of lean meat. As the result of the negative control was rated as C, evaluation was categorized as very good (A), good (B), fair, the same as Control 1 (C), and poor (D), and an average of the scores of the 8 panelists was calculated. The results are shown in Table 37.

TABLE 37

| | Negative control | Preparation Example 8-added group |
|---|---|---|
| Softness of lean meat | C | A |

As a result, the heated squid marinated with the marinade of Preparation Example 8-added group was considerably enhanced in softness of lean meat, compared to that marinated with the marinade of the negative control.

In addition, when squid ears were used as a material, the heated squid marinated with the marinade of the Preparation Example 8-added group was suppressed in warping of the ear portion due to heating. From the results, it was considered that the toughening of lean meat was prevented by suppressing the shrinkage of meat due to the marinating with the marinade of the Preparation Example 8-added group. In addition, the heated squid marinated with the marinade of the Preparation Example 8-added group was preferable in terms of yield.

From the above results, it was confirmed that a marinade prepared by adding yeast cells further subjected to conventional treatment to the marinade containing sodium bicarbonate known to softening lean meat has a more synergistic effect of softening lean meat than the marinade containing sodium bicarbonate.

Experimental Example 32

(Evaluation as Quality Improving Material for Food 15)

Effects exhibited when a hamburger patty was mixed with the sample of Preparation Example 8 were investigated. A hamburger patty was prepared by mixing 50 parts by mass of a mixture of minced pork and chicken meats, 25 parts by mass of chopped onion, 15 parts by mass of water, table salt, and a hint of pepper. The sample of Preparation Example 8 was added to the hamburger patty at the ratio shown in Table 38, and mixed. Afterward, the resulting patty mixture was shaped in a flat circle, and then a hamburger was prepared according to a conventional method.

TABLE 38

| | Blending ratio (parts by mass) | | |
|---|---|---|---|
| Food ingredient | Negative control | Preparation Example 8, 0.4% by mass-added group | Preparation Example 8, 1.0% by mass-added group |
| Hamburger patty | 100 | 99.6 | 99.0 |
| Sample of Preparation Example 8 | — | 0.4 | 1.0 |

Subsequently, the resulting hamburgers were tasted by 8 panelists to perform sensory evaluation. An evaluation item was the softness of lean meat. As the result of the negative control was rated as C, the evaluation was categorized as very good (A), good (B), fair, the same as Control 1 (C), and poor (D), and the averages of the scores of the 8 panelists were calculated. The results are shown in Table 39.

TABLE 39

|  | Negative control | Preparation Example 8, 0.4% by mass-added group | Preparation Example 8, 1.0% by mass-added group |
|---|---|---|---|
| Softness of lean meat | C | B | A |

As a result, compared to the negative control, in the group to which the sample of Preparation Example 8 was added, lean meat was soft. Also, a hamburger of a group to which the sample of Preparation Example 8 was added at 1.0% by mass, which has a larger addition amount of the sample of Preparation Example 8 was further enhanced in softness than a hamburger of a group to which 0.4% by mass of Preparation Example 8 was added. Also, compared to the negative control, in the sample of Preparation Example 8-added group, yield was enhanced.

INDUSTRIAL APPLICABILITY

According to the present invention, a more effective method of improving the taste of yeast cells can be provided. Also, a quality improving material for food containing yeast cells with improved taste as an active ingredient can be provided.

The invention claimed is:

1. A method for producing a yeast composition comprising:
   obtaining a residue generated after extracting yeast cells by a hydrothermal treatment method;
   reacting a protease with the residue,
   adding an emulsifier to the residue in an amount of 0.01 to 0.1% by mass before or after the reaction of the protease; and
   washing the residue with water after the reaction of the protease and the addition of the emulsifier;
   wherein the emulsifier has an Hydrophile-Lipophile Balance value of 2.8 to 14; and
   the yeast composition contains proteins at 40% by mass or more.

2. The method according to claim 1, wherein the emulsifier is one or a mixture of two or more types of compounds selected from the group consisting of glycerin fatty acid esters, sorbitan fatty acid esters, propylene glycol fatty acid esters, sucrose fatty acid esters, lecithins and saponins.

3. The method according to claim 1, wherein the protease is an endo-type protease.

4. The method according to claim 3, wherein the endo-type protease is derived from *Bacillus amyloliquefaciens*.

5. A food composition comprising the yeast composition produced by the method according to claim 1.

6. The food composition according to claim 5, comprising:
   proteins at 25% by mass or more, β-glucans at 10% by mass or more, and dietary fiber at 25% by mass or more.

7. A powder mixture, comprising:
   the food composition according to claim 5.

8. Batter, comprising:
   the food composition according to claim 5.

9. Fried food, comprising:
   the food composition according to claim 5.

10. A softener for meat or seafood, comprising:
    the food composition according to claim 5.

11. A method of softening meat or seafood, comprising:
    contacting the food composition according to claim 5 with meat or seafood.

12. A method for preventing syneresis or oil separation of processed food, comprising:
    contacting the food composition according to claim 5 with a food material.

13. The method according to claim 1, further comprising:
    reacting a cellulase with the residue.

* * * * *